US011844515B2

(12) United States Patent
Voss et al.

(10) Patent No.: US 11,844,515 B2
(45) Date of Patent: Dec. 19, 2023

(54) SUTURING SYSTEMS AND METHODS

(71) Applicant: Abbott Cardiovascular Systems, Inc., Santa Clara, CA (US)

(72) Inventors: Laveille Kao Voss, Belmont, CA (US); Aaron M. Fortson, Fremont, CA (US); Wouter E. Roorda, Palo Alto, CA (US); Stephanie Henze, San Mateo, CA (US); Kristopher M. Konawalik, San Francisco, CA (US); Leah M. Davis, San Francisco, CA (US)

(73) Assignee: Abbott Cardiovascular Systems, Inc., Santa Clara, CA (US)

( * ) Notice: Subject to any disclaimer, the term of this patent is extended or adjusted under 35 U.S.C. 154(b) by 414 days.

(21) Appl. No.: 17/130,801

(22) Filed: Dec. 22, 2020

(65) Prior Publication Data
US 2021/0106328 A1 Apr. 15, 2021

Related U.S. Application Data

(60) Continuation of application No. 16/936,781, filed on Jul. 23, 2020, which is a continuation of application
(Continued)

(51) Int. Cl.
*A61B 17/062* (2006.01)
*A61B 17/06* (2006.01)
(Continued)

(52) U.S. Cl.
CPC ...... *A61B 17/0625* (2013.01); *A61B 17/0057* (2013.01); *A61B 17/0469* (2013.01);
(Continued)

(58) Field of Classification Search
CPC ............ A61B 17/0057; A61B 17/0469; A61B 17/0482; A61B 17/0491; A61B 17/06161;
(Continued)

(56) References Cited

U.S. PATENT DOCUMENTS 2,544,282 A 3/1951 Sinclair et al.
2,589,499 A 3/1952 Varnall
(Continued)

OTHER PUBLICATIONS

Notice of Allowance received for U.S. Appl. No. 13/610,598, dated Feb. 12, 2016.
(Continued)

*Primary Examiner* — Robert A Lynch
(74) *Attorney, Agent, or Firm* — Workman Nydegger; Randy Shen

(57) ABSTRACT

A medical device including an elongate member extending from a proximal end toward a distal end, the elongate member having a lumen with a longitudinal axis, a hub portion towards the proximal end of the elongate member and configured for a user to hold and manipulate a position of the elongate member, a base portion including a first groove and a second groove separated by an opening, and two wings disposed towards a distal end of the medical device, the two wings being opposite each other across the longitudinal axis and on opposite sides of the base portion, wherein, the two wings are configured to move in relation to the longitudinal axis and wherein each wing has an elongate slot having a closed first end at a location between the base portion and a peripheral end of the wing.

13 Claims, 16 Drawing Sheets

Related U.S. Application Data

No. 15/949,642, filed on Apr. 10, 2018, now Pat. No. 10,743,864, which is a continuation of application No. 15/162,030, filed on May 23, 2016, now abandoned, which is a division of application No. 13/610,598, filed on Sep. 11, 2012, now Pat. No. 9,345,474.

(51) Int. Cl.
*A61B 17/04* (2006.01)
*A61B 17/00* (2006.01)

(52) U.S. Cl.
CPC ........ *A61B 17/0491* (2013.01); *A61B 17/062* (2013.01); *A61B 17/06161* (2013.01); *A61B 2017/00663* (2013.01); *A61B 2017/047* (2013.01); *A61B 2017/0472* (2013.01); *A61B 2017/06042* (2013.01)

(58) Field of Classification Search
CPC .............. A61B 17/062; A61B 17/0625; A61B 2017/00637; A61B 2017/047; A61B 2017/0472; A61B 2017/06042
See application file for complete search history.

(56) References Cited

U.S. PATENT DOCUMENTS

| | | |
|---|---|---|
| 2,829,812 A | 4/1958 | Wilson, Jr. |
| 4,011,870 A | 3/1977 | Goldstein |
| 4,373,530 A | 2/1983 | Kilejian |
| 4,414,908 A | 11/1983 | Eguchi et al. |
| 4,614,187 A | 9/1986 | Mulhollan et al. |
| 4,643,341 A | 2/1987 | Hostetler |
| 4,898,157 A | 2/1990 | Messroghli et al. |
| 4,965,426 A | 10/1990 | Colombo |
| 4,981,476 A | 1/1991 | Aichlmayr et al. |
| 5,002,550 A | 3/1991 | Li |
| 5,024,666 A | 6/1991 | Pituch |
| 5,100,421 A | 3/1992 | Christoudias |
| 5,188,636 A | 2/1993 | Fedotov |
| 5,242,426 A | 9/1993 | Pituch |
| 5,320,632 A | 6/1994 | Heidmueller |
| 5,330,488 A | 7/1994 | Goldrath |
| 5,354,298 A | 10/1994 | Lee et al. |
| 5,365,029 A | 11/1994 | Makihara |
| 5,374,275 A | 12/1994 | Bradley et al. |
| 5,415,315 A | 5/1995 | Ramirez |
| 5,417,701 A | 5/1995 | Holmes |
| 5,458,609 A * | 10/1995 | Gordon .............. A61B 17/0625 606/147 |
| 5,469,964 A | 11/1995 | Bailey |
| 5,476,470 A | 12/1995 | Fitzgibbons, Jr. |
| 5,480,407 A | 1/1996 | Wan et al. |
| 5,601,575 A | 2/1997 | Measamer et al. |
| 5,746,757 A | 5/1998 | McGuire |
| 5,779,719 A | 7/1998 | Klein et al. |
| 5,814,065 A | 9/1998 | Diaz |
| 5,891,159 A | 4/1999 | Sherman et al. |
| 5,972,005 A | 10/1999 | Stalker et al. |
| 6,036,699 A | 3/2000 | Andreas et al. |
| 6,048,351 A | 4/2000 | Gordon et al. |
| 6,464,707 B1 | 10/2002 | Bjerken |
| 6,673,091 B1 | 1/2004 | Shaffer et al. |
| 6,712,828 B2 | 3/2004 | Schraft et al. |
| 6,730,102 B1 | 5/2004 | Burdulis et al. |
| 6,743,241 B2 * | 6/2004 | Kerr .................. A61B 17/0057 606/139 |
| 6,877,352 B1 | 4/2005 | David |
| 7,188,756 B1 | 3/2007 | Storm |
| 7,909,804 B2 | 3/2011 | Stats |
| 8,753,357 B2 | 6/2014 | Roorda et al. |
| 8,864,778 B2 | 10/2014 | Fortson et al. |
| 9,192,369 B2 | 11/2015 | Bittenson |
| 9,345,474 B2 | 5/2016 | Voss et al. |
| 9,345,475 B2 | 5/2016 | Voss et al. |
| 9,402,609 B2 | 8/2016 | Ramos Clamote |
| 9,408,600 B2 | 8/2016 | Melsheimer et al. |
| 9,446,190 B2 | 9/2016 | Miller |
| 10,194,903 B2 | 2/2019 | Voss et al. |
| 2002/0013603 A1 | 1/2002 | Green |
| 2002/0095164 A1 | 7/2002 | Andreas et al. |
| 2003/0029014 A1 | 2/2003 | Samuel |
| 2003/0158604 A1 | 8/2003 | Cauthen et al. |
| 2003/0171718 A1 | 9/2003 | Delegge et al. |
| 2003/0233119 A1 | 12/2003 | Tiedemann |
| 2004/0138613 A1 | 7/2004 | Reid |
| 2004/0158309 A1 | 8/2004 | Wachter et al. |
| 2005/0038500 A1 | 2/2005 | Boylan et al. |
| 2005/0125013 A1 | 6/2005 | Kessler |
| 2007/0016135 A1 | 1/2007 | Kanner et al. |
| 2007/0135824 A1 | 6/2007 | O'Brien |
| 2007/0276488 A1 | 11/2007 | Wachter et al. |
| 2008/0097480 A1 | 4/2008 | Schorr et al. |
| 2008/0243147 A1 | 10/2008 | Hamilton et al. |
| 2008/0312740 A1 | 12/2008 | Wachter et al. |
| 2009/0048615 A1 * | 2/2009 | McIntosh ........... A61B 17/0491 606/232 |
| 2009/0062743 A1 | 3/2009 | Rotella et al. |
| 2009/0177031 A1 | 7/2009 | Surti et al. |
| 2010/0170812 A1 | 7/2010 | Odierno |
| 2011/0106142 A1 | 5/2011 | Van et al. |
| 2012/0316580 A1 | 12/2012 | Belman et al. |
| 2014/0074124 A1 | 3/2014 | Voss et al. |
| 2014/0074126 A1 | 3/2014 | Voss et al. |
| 2015/0119906 A1 | 4/2015 | Bagaoisan et al. |
| 2017/0020518 A1 | 1/2017 | Voss et al. |
| 2018/0221020 A1 | 8/2018 | Voss et al. |
| 2019/0117221 A1 | 4/2019 | Voss et al. |

OTHER PUBLICATIONS

Notice of Allowance received for U.S. Appl. No. 13/610,602, dated Feb. 12, 2016.
Notice of Allowance received for U.S. Appl. No. 15/162,085, dated Sep. 26, 2018.
Notice of Allowance received for U.S. Appl. No. 15/949,642, dated Apr. 13, 2020.
Office Action received for U.S. Appl. No. 13/610,595, dated Feb. 4, 2015.
Office Action received for U.S. Appl. No. 13/610,595, dated Jul. 28, 2014.
Office Action received for U.S. Appl. No. 13/610,595, dated Mar. 3, 2017.
Office Action received for U.S. Appl. No. 13/610,595, dated May 4, 2016.
Office Action received for U.S. Appl. No. 13/610,595, dated Oct. 20, 2015.
Office Action received for U.S. Appl. No. 13/610,598, dated Apr. 21, 2015.
Office Action received for U.S. Appl. No. 13/610,598, dated Oct. 21, 2015.
Office Action received for U.S. Appl. No. 15/162,030, dated Jan. 10, 2018.
Office Action received for U.S. Appl. No. 15/949,642, dated Dec. 2, 2019.
Office Action received for U.S. Appl. No. 15/949,642, dated Feb. 12, 2019.
Office Action received for U.S. Appl. No. 16/223,827, dated Jul. 23, 2020.
U.S. Appl. No. 13/443,659, filed Apr. 10, 2012, Fortson et al.
U.S. Appl. No. 13/610,602, filed Sep. 11, 2012, Voss et al.

* cited by examiner

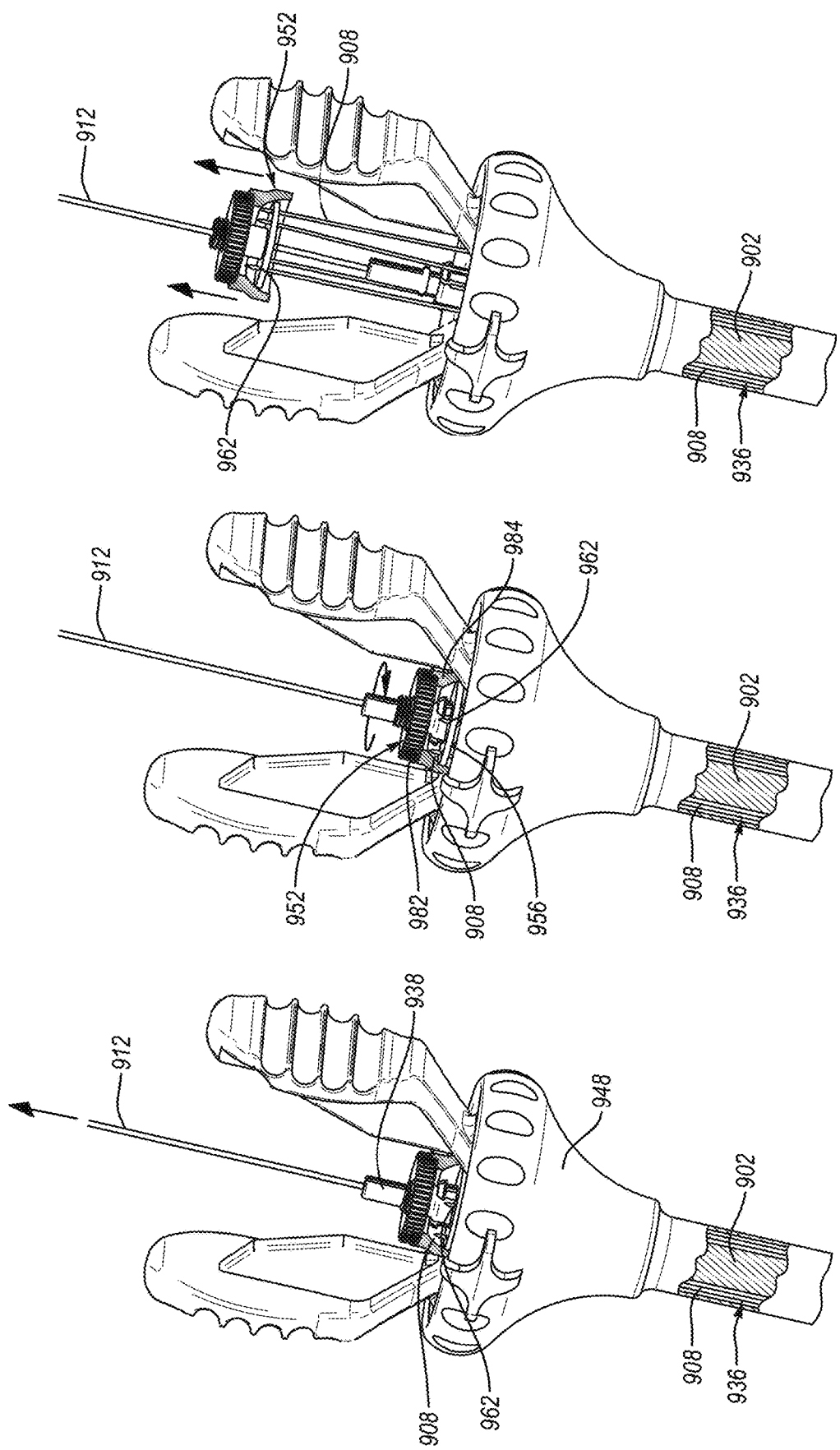

SUTURING SYSTEMS AND METHODS

CROSS-REFERENCE TO RELATED APPLICATIONS

This application is a continuation of U.S. patent application Ser. No. 16/936,781, filed Jul. 23, 2020, which is a continuation of U.S. patent application Ser. No. 15/949,642, filed Apr. 10, 2018, which is a continuation of U.S. patent application Ser. No. 15/162,030, entitled "Needle Removal Devices, Systems, and Methods", filed May 23, 2016, which is a divisional of U.S. patent application Ser. No. 13/610,598, entitled "Needle Removal Devices, Systems, and Methods", filed Sep. 11, 2012, now U.S. Pat. No. 9,345,474, the disclosures of which are incorporated herein by this reference.

BACKGROUND OF THE INVENTION

1. The Field of the Invention

Embodiments of the invention relate generally to devices, systems, and methods devices for removing needles from systems or devices used to close openings in body lumens. More particularly, the present invention relates to devices, systems, and methods for removing needles from systems or devices used for closure of arterial and venous puncture sites accessed through a tissue tract.

2. The Relevant Technology

A number of diagnostic and interventional vascular procedures are now performed translumenally. A catheter is introduced to the vascular system at a convenient access location and guided through the vascular system to a target location using established techniques. Such procedures require vascular access, which is usually established using the well-known Seldinger technique. Vascular access is generally provided through an introducer sheath, which is positioned to extend from outside the patient's body into the vascular lumen. When vascular access is no longer required, the introducer sheath is removed and bleeding at the puncture site stopped.

One common approach for achieving hemostasis (the cessation of bleeding) is to apply external force near and upstream from the puncture site, typically by manual compression. However, the use of manual compression suffers from a number of disadvantages. For example, the manual compression procedure is time consuming, frequently requiring one-half hour or more of compression before hemostasis is achieved. Additionally, such compression techniques rely on clot formation, which can be delayed until anticoagulants used in vascular therapy procedures (such as for heart attacks, stent deployment, non-optical PTCA results, and the like) wear off. The anticoagulants may take two to four hours to wear off, thereby increasing the time required before completion of the manual compression procedure.

Further, the manual compression procedure is uncomfortable for the patient and frequently requires analgesics to be tolerable. Moreover, the application of excessive pressure can at times totally occlude the underlying blood vessel, resulting in ischemia and/or thrombosis. Following manual compression, the patient typically remains recumbent from four to as much as twelve hours or more under close observation to assure continued hemostasis. During this time, renewed bleeding may occur, resulting in blood loss through the tract, hematoma and/or pseudo-aneurysm formation, as well as arteriovenous fistula formation. These complications may require blood transfusions and/or surgical intervention.

The incidence of complications from the manual compression procedure increases when the size of the introducer sheath grows larger, and/or when the patient is anticoagulated. The compression technique for arterial closure can be risky, and is expensive and onerous to the patient. Although trained individuals can reduce the risk of complications, dedicating such personnel to this task is both expensive and inefficient. Nonetheless, as the number and efficacy of translumenally performed diagnostic and interventional vascular procedures increase, the number of patients requiring effective hemostasis for a vascular puncture continues to increase.

To overcome the problems associated with manual compression, the use of bioabsorbable sealing bodies is another example approach that has been proposed to achieve hemostasis. Generally, the use of bioabsorbable sealing bodies relies on the placement of a thrombogenic and bioabsorbable material, such as collagen, at the superficial arterial wall over the puncture site. While potentially effective, the use of bioabsorbable material suffers from a number of drawbacks. For example, bioabsorbable sealing bodies may lack a solid mechanical attachment of the sealing body to the tissue. Due to the lack of a solid mechanical attachment, the sealing body can wander within the tissue tract or move out of the puncture site, thus causing late bleeds. Conversely, if the sealing body wanders and intrudes too far into the arterial lumen, due to the lack of a solid mechanical attachment, intravascular clots and/or collagen pieces with thrombus attached can form and embolize downstream, causing vascular occlusion.

In addition to not having a solid mechanical attachment to the tissue, the sealing bodies may rely upon expandable materials to achieve hemostasis. Again, the expandable materials lack the security of a hard mechanical closure, thus potentially causing late bleeds and prolonging hemostasis.

A further approach to achieving hemostasis is to use a suture to close a puncture site. Although difficult to suture manually, suture applying devices can be used to appropriately place a suture for closing a puncture site. One example suture applying device has a shaft carrying a pair of needles near its distal end. The needles are joined together by a length of suture. The shaft is used to introduce the needles into a lumen of a body structure and the needles pushed back through the lumen wall on either side of a puncture site. After the needles have passed back through the tissue, they are captured on the shaft and drawn proximally away from the body structure. Drawing the needles outward leaves a loop of suture behind to close the puncture site. The loop of suture can then be tied in a knot to complete the closure. Suture applying devices address many disadvantages associated with the use of external force (e.g., digital compression and with the use of bioabsorbable sealable bodies to achieve hemostasis.

However, the use of suture applying devices also has a number of inefficiencies. Typically, to access a suture in a manner that it can be tied off, the needle must be fully removed from the shaft and other components subsequently moved out of the way. However, after needle deployment, suture applying devices are often configured to draw needles proximally only to a point where they are partially exposed at the proximal end of the shaft. To remove needles from the shaft completely, an operator has to use manual force to individually grab the proximal end of each needle (e.g., with a hemostat) and draw it further proximally while also securely holding the shaft. The amount of force required to further draw the needle proximally can sometimes be quite large (and potentially unacceptable).

Some suture applying devices have a separate internal needle holder that can be used to receive a partially exposed needle. The needle holder assists an operator in drawing the needle proximally until the distal end of the needle exits the proximal end of the shaft. However, needle holders often do not sufficiently grip a needle such that it can be efficiently drawn proximally. Additionally, the leverage obtained from using a needle holder is often insufficient to remove a needle from challenging (e.g., calcified or scarred) tissue anatomy.

For at least these reasons, it would be desirable to provide devices and methods for more efficiently removing needles from a suture applying device. It would be particularly desirable to provide devices and methods for efficiently removing needles from a suture applying device used to suture a puncture site associated with a percutaneous vascular procedure.

BRIEF SUMMARY OF THE INVENTION

Embodiments of the invention relate generally to devices, systems, and methods for removing needles from systems or devices used to close openings in body lumens. In an embodiment, a needle removal device may include a base member configured to be selectively positioned substantially adjacent a proximal portion of a suturing system. The proximal portion of the suturing system may include a plurality of needle lumens extending. The needle removal device may also include a plurality of needle receptacles at least partially defined by the base member. The needle receptacles may be positioned and configured to generally correspond to the needle lumens of the suturing device. The needle receptacles may be further configured to selectively receive and grasp onto one or more needles extending proximally from the needle lumens of the suturing device.

In an embodiment, the base member may be at least semi-flexible and the needle receptacles may be formed in a bottom surface of the base member. Grooves may be formed in an upper surface of the base member and may be in communication with the needle receptacles. A pair of tabs may be attached to opposite ends of the base member. The tabs may be configured to move the needle removal element between a receiving position, wherein at least a portion of the needles are moveable within the needle receptacles, and a grasping position, wherein the tabs flex the base member such that the grooves grasp the needles between opposing sidewalls of the grooves to secure the needles within the needle receptacles.

In another embodiment, the base member may comprise a generally cylindrical body and the needle receptacles extend at least partially through the body. A plurality of slots that traverse at least a portion of the needle receptacles may be formed in a lateral surface of the body. The needles may include notched portions configured and positioned to engage with the slots to lock the needles in the needle receptacles.

In an embodiment, a suture system may include a plurality of needles. One or more sutures may have an end attached to one of the needles. The system may also include a guide body having a proximal end, a distal end, a central lumen, one or more suture lumens configured to receive at least a portion of the one or more sutures, and a plurality of needle lumens configured to receive the needles. A shaft may be moveably positioned within the guide body. The shaft may be operably connected to the needles such that proximal movement of the shaft draws the needles into the needle lumens. The system may also include a needle removal device positioned substantially adjacent the proximal end of the guide body. The needle removal device may include a base member and a plurality of needle receptacles generally corresponding to the plurality of needle lumens. The needle removal device may be configured and positioned to selectively receive and remove one or more of the needles from the needle lumens.

In an embodiment, a method for removing one or more needles from a suturing system may include positioning a needle removal device substantially adjacent a proximal end of the suturing system. The method may also include drawing the needles proximally through the suturing system until at least the tips of the needles exit from the proximal end of the suturing system. The tips of the needles may then be received within needle receptacles formed within the needle removal device. The needles may then be secured within the needle receptacles. Finally, the needle removal device may be moved proximally relative to the suturing system to remove the needles from the suturing system.

These and other advantages and features of the present invention will become more fully apparent from the following description and appended claims, or may be learned by the practice of the invention as set forth hereinafter.

BRIEF DESCRIPTION OF THE DRAWINGS

To further clarify at least some of the advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which:

FIGS. 10A-10C illustrate exemplary steps for removing needles from the suturing system shown in FIG. 9A with the needle removal device.

DETAILED DESCRIPTION OF THE PREFERRED EMBODIMENTS

As used herein, the term "distal" is generally defined as in the direction of the patient or away from a user of a device. In the context of a medical device intervention with or through a vessel wall, "distal" herein refers to the interior or the lumen side of the vessel wall. Conversely, "proximal" generally means away from the patient or toward the user. In the context of a medical device intervention with or through a vessel wall, "proximal" herein refers to the exterior or outer side of the vessel wall.

The term "hemostasis" is herein used to mean the arrest of bleeding or substantially blocking flow of blood outwardly from a vessel lumen while the vessel lumen is pressurized or sustaining physiological blood flow. This amount of blockage or occlusion to flow is further defined such that the blood loss which is experienced is less than an amount which would affect procedural methods or outcomes according to a physician user of a device of ordinary skill in the art. In other words, "hemostasis" is not intended to mean only "total hemostasis" such that there is a total lack of blood loss. Rather, the term is used to also mean "procedural hemostasis" as a relative term in its use among physicians of ordinary skill.

The term "suturing" is herein intended to include the process of joining two surfaces or edges together with a suture such as a thread of material (either polymeric or natural), gut, wire, or the like or so as to close an aperture, opening, or wound, or join tissues.

Figure 1A:
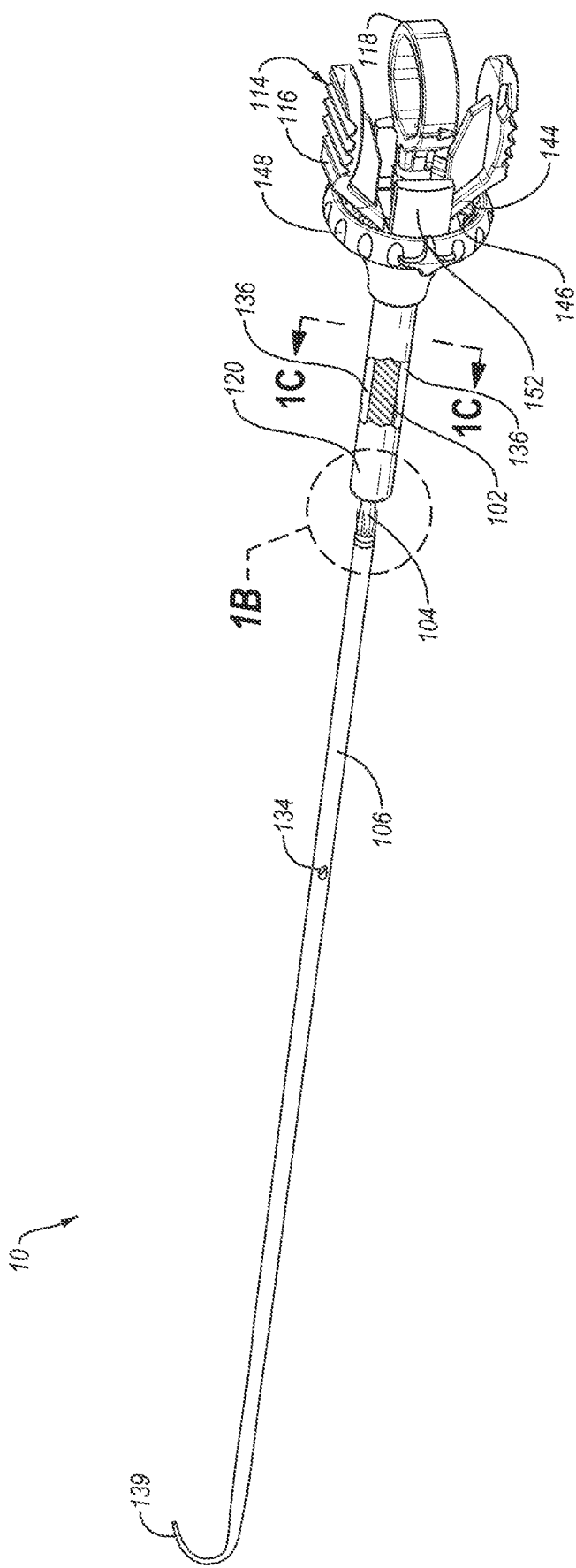
FIG. 1A illustrates a side perspective view of a suturing system according to an embodiment.
Figure 1B:
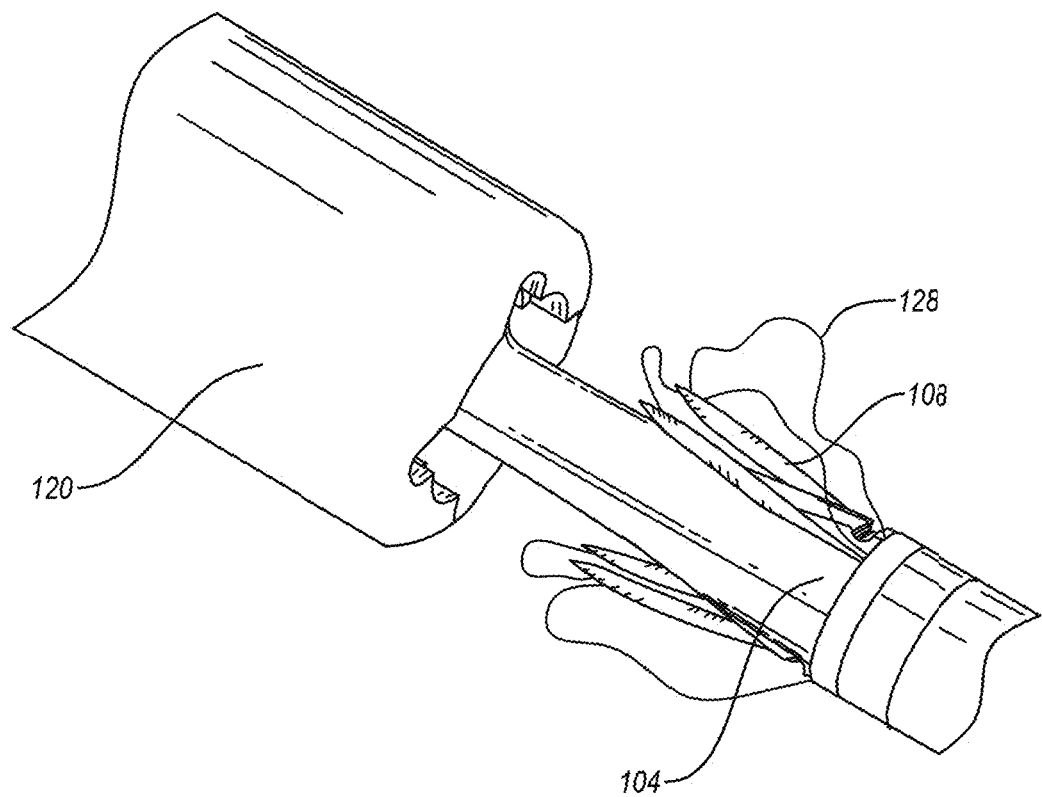
FIG. 1B illustrates a detailed view of the needle guide of the suturing device of FIG. 1A taken along line 1B-1B.

Referring to FIG. 1A and FIG. 1B, a suturing system 10 may be provided to close openings in body tissues. The suturing system 10 may comprise a guide body 102, a needle guide 104 secured to a distal end of the guide body 102, and a flexible tube 106 secured to a distal end of the needle guide 104. A plurality of needles 108 may be mounted with their distal ends in a support holster (not shown) within the flexible tube 106. In an embodiment, a moveable needle deployment shaft 112 (shown in FIG. 2B) may be operatively connected to the needles 108. For example, the needle deployment shaft 112 may be attached to the support holster and may be moveably positioned within a central lumen 122 (shown in FIG. 1C) that extends at least partially through the flexible tube 106, the needle guide 104, and the guide body 102. As shown further in regard to FIGS. 2A-2D, the guide body 102 of the suturing system 10 may be introduced within a percutaneous tissue tract leading to a puncture site with the flexible tube 106 positioned within a vessel. When the needle deployment shaft 112 is moved proximally relative to the guide body 102, the needles 108 may be drawn proximally through the flexible tube 106, out the needle guide 104 and toward the guide body 102. The needles 108 may carry suture lengths 128 (shown in FIG. 1B) which may be used to close the puncture site. As the needles 108 extend from the needle guide 104, the needles 108 may pass through tissue positioned between the needle guide 104 and the guide body 102. The guide body 102 may then capture the needles 108 and route them toward the user.

A handle assembly 114 may be attached to a proximal end of the guide body 102. The handle assembly 114 may include interlock wings 116, a needle removal device 152, and a handle 118. The handle 118 may be attached to a proximal end of the needle deployment shaft 112 and can be pulled proximally in order to actuate the needle deployment shaft 112. A sheath 120 may also be rotatably received over the guide body 102. The sheath 120 may be sized to be introducible through the percutaneous tissue tract. The sheath 120 may be inflexible or flexible and formed at least partially from metal, a hard plastic or polymer material, or other suitable materials.

Figure 1C:
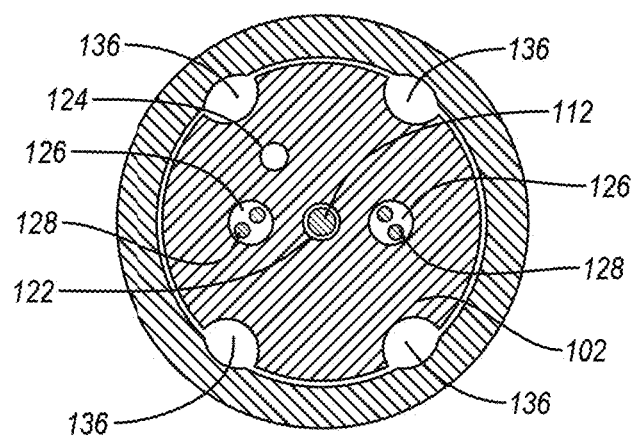
FIG. 1C illustrates a cross-sectional view of the suturing system of FIG. 1A taken along line 1C-1C.

As best shown in FIG. 1C, the guide body 102 may define one or more axial lumens or channels therein. For example, the central axial lumen 122 may be provided for slidably receiving the needle deployment shaft 112. The guide body 102 may also include one or more blood detection lumens 124 and one or more suture lumens 126 that pass therethrough. The one or more blood detection lumens 124 may be configured for receiving blood from the vessel to assist in positioning the suturing system 10. The one or more suture lumens 126 may be configured to receive the suture lengths 128 attached to the needles 108. In other embodiments, the blood detection lumen 124 may be omitted.

The guide body 102 may further include a plurality of needle lumens 136. The needle lumens 136 may be axially aligned and circumferentially spaced about the periphery of the guide body 102. In other embodiments, the needle lumens 136 may be configured to extend through the guide body 102. In yet other embodiments, the needle lumens 136 may be configured to extend along paths wherein the needle lumens 136 exit along a single side of the guide body 102 as described, for example, in U.S. Patent Application entitled "Removing Needles from a Suturing Device," Ser. No. 13/610,595, filed on the same day, the disclosure of which is incorporated herein in its entirety. The needles 108 may enter the distal ends of the needle lumens 136 after the needles 108 exit the needle guide 104.

Referring again to FIG. 1A, the flexible tube 106 may be formed from a flexible plastic, polymer, metal, combinations thereof, or any other suitable material. The flexible tube 106 may be generally circular in cross-sectional geometry and may include a guide wire lumen (not shown) and the central lumen (not shown) configured to house the support holster (not shown) and the needles 108. The flexible tube 106 may further include a guide wire exit port 134 configured to allow a guide wire that is advanced proximally through a guide wire lumen (not shown) to exit from a side of the flexible tube 106. Optionally, the flexible tube 106 may include a distal J-tip 139 for atraumatic tracking through vessels or other body lumens. In other embodiments, the distal J-tip 139 may be omitted.

Construction of the handle assembly 114 will now be described. A stem 138 (shown in FIG. 2B) may be formed between the interlock wings 116 for receiving the handle 118. The stem 138 may include a key 130 that is received into a slot (not shown) in the handle 118. Such a configuration may allow the handle 118 to be slid into the stem 138 with the key being received into the slot. The handle 118 may be rotated in a clockwise direction to secure the handle 118 to the stem and prevent axial translation of the needle deployment shaft 112. To move the needle deployment shaft 112 and deploy the needles 108, the handle 118 may be rotated in a counter-clockwise direction so that the key may be pulled from the slot. The handle 118 may then be proximally moved to deploy the needles 108.

The handle assembly 114 may be securely attached to the guide body 102 so that the sheath 120 may be rotated relative to the guide body 102 when holding the handle assembly 114. The handle assembly 114 may be securely fastened to the guide body 102 by gluing, molding, and the like. In other embodiments, the handle assembly 114 may be formed as an integral part of the guide body 102. The handle assembly 114 may also include a plurality of tubes (not shown) aligned with the blood detection lumen 124 and the one or more suture lumens 126. At least a portion of the suture lengths may pass through one or more of the tubes.

The interlock wings 116 may each include a detent 144 for engaging a pair of grooves 146 in a hub 148 of the sheath 120. The interlock wings 116 may be constructed of a resilient material (e.g., polycarbonate) so that the interlock wings 116 may be pressed together to remove the detents 144 from the grooves 146. Upon removal of the detents 144 from the grooves 146, the sheath 120 may be rotated relative to the guide body 102 by maintaining a grip on the interlock wings 116 with one hand and rotating the hub 148 with the other hand. In other embodiments, the interlock wings 116 and the hub 148 may allow a physician or other user to hold and manipulate the suturing system 10. For example, the physician can hold on to the hub 148 when inserting and withdrawing the suturing system 10 from a puncture site.

Referring now to FIGS. 1A and 1C, the central lumen 122 may extend from the flexible tube 106, through the needle guide 104, through the guide body 102 and into the stem 138 of the handle assembly 114. The needle deployment shaft 112 may run the length of the central lumen 122. Accordingly, the handle 118 may be proximally moved to move the needle deployment shaft 112 through the central lumen 122 which in turn moves the needles 108. The one or more suture lumens 126 may run generally parallel or non-parallel to the central lumen 122. The suture lengths 128 may pass through the one or more suture lumens 126. In one embodiment, the suture lengths 128 may be configured in the form of the loop with the free ends being attached to the needles 108 and with the looped end passing outside the suturing system 10 through the tube (not shown). Such a configuration facilitates management of the suture lengths 128 during insertion of the suturing system 10 to a puncture site and during movement of the needles 108 to suture the vessel wall. As the needles 108 are proximally advanced through the guide body 102, the suture lengths 128 are drawn distally through the suture lumen 126 where they are completely removed from the suture lumen 126 upon full deployment of the needles 108 wherein the tips of the needles 108 exit the hub 148 and are received by the needle removal device 152 positioned at the proximal end of the guide body 102. The needle removal device 152 may be configured to selectively grasp or pinch the needles 108 exiting from the hub 148 and to draw the needles 108 proximally out of the guide body 102 until the suture lengths 128 are available to a user to be tied over the puncture site.

As shown in FIG. 1A, the needle removal device 152 may be positioned at least partially within the hub 148. In other embodiments, the needle removal device 152 may be selectively positioned distally or proximally of the hub 148.

Figure 1D:
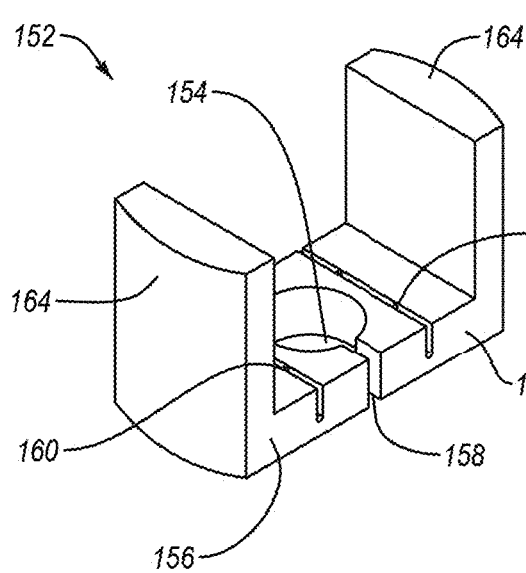
FIG. 1D illustrates a top perspective view of the needle removal device removed from the suturing system shown in FIG. 1A.
Figure 1E:
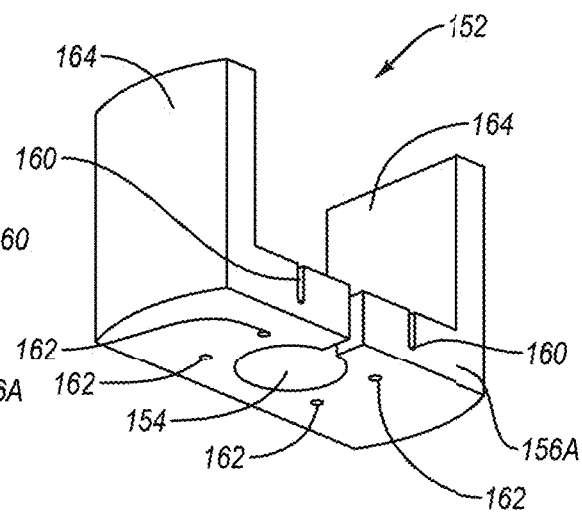
FIG. 1E illustrates a bottom perspective view of the needle removal device shown in FIG. 1D.

FIGS. 1D and 1E show the needle removal device 152 removed from the suturing system 10. The needle removal device 152 may include a base portion 156 and a pair of tabs 164 attached at opposite ends of the base portion 156. The needle removal device 152 may be made from polymers, polymeric composites, titanium, stainless steel, metal alloys, combinations thereof, or any other suitable materials. As shown, a central aperture 154 may be formed in the base portion 156. The central aperture 154 may be configured to allow the stem 138 of the handle assembly 114 to pass through the base portion 156 such that the needle removal device 152 may be selectively positioned between the guide body 102 and the handle 118. The central aperture 154 may also be configured to receive the needle deployment shaft 112 such that the needle deployment shaft 112 may selectively be drawn through the needle removal device 152. Such a configuration allows the needle deployment shaft 112 and the needle removal device 152 to move axially relative to one another.

In another embodiment, the needle removal device 152 may further include a disengagement slot 158 extending between the aperture 154 and a first side surface 156A of the base portion 156. The disengagement slot 158 may be configured to help the needle removal device 152 to be selectively removed from the needle deployment shaft 112. In other embodiments, the disengagement slot 158 may be omitted.

As shown, a pair of grooves 160 may be formed in an upper surface of the base portion 156. Each of the grooves 160 may include a bottom portion and opposing sidewalls. As illustrated in FIG. 1D, the grooves 160 may be substantially linear and parallel to one another. In other embodiments, the grooves 160 may be substantially non-linear and/or non-parallel to one another. As shown, each of the grooves 160 may have a length that extends along an axis of the groove 160 between the first side surface 156A and a second side surface 156B of the base portion 156. In other embodiments, the length of one or more of the grooves 160 may extend only partially between the first side surface 156A and the second side surface 156B.

As shown, each of the grooves 160 may also have a depth extending between the upper surface of the base portion 156 and the bottom portion of the groove 160. In another embodiment, the depth of one or more of the grooves 160 may be constant. In other embodiments, the depth of one or more of the grooves 160 may vary. For example, the one or more of the grooves 160 may include a deeper portion and a shallower portion. The depth of one or more of the grooves 160 may be about twenty five (25) percent to ninety five (95) percent; about thirty five (35) percent to eighty five (85) percent; about forty five (45) percent to seventy five (75) percent of a thickness of the base portion 156 defined between the upper and lower surfaces of the base portion 156. In other embodiments, the depth of one or more grooves 160 may be larger or smaller relative to the thickness of the base portion 156.

Each of the grooves 160 may also include a width extending between the opposing sidewalls of the groove 160. The opposing sidewalls may be substantially planar and perpendicular to the bottom surface of the base portion 156. In other embodiments, the sidewalls may be substantially non-perpendicular to the bottom surface of the base portion 156. In other embodiments, the sidewalls may be substantially non-planar, concavely curved, or have other suitable configurations. In other embodiments, the width of the grooves 160 may be constant along the length of the grooves 160. In yet other embodiments, the width of the grooves 160 may vary along the length of the grooves 160. For example, the grooves 160 may include narrower and wider portions.

As shown in FIG. 1D, a plurality of needle receptacles 162 may be formed in the base portion 156. The needle receptacles 162 may extend between the bottom surface of the base portion 156 and the bottom portion of the grooves 160. One or more of the needle receptacles 162 may have a generally cylindrical geometric shape, generally conical geometric shape, generally oval geometric shape, or any other suitable geometric shape. The needle receptacles 162 may be configured and positioned in the base portion 156 to generally correspond to the needle lumens 136 exiting the proximal end of the guide body 102. Such a configuration allows the needles 108 to be selectively received within the needle receptacles 162 when the needles 108 exit the needle lumens 136 of the guide body 102. While four needle receptacles 162 are shown surrounding the central aperture 154, three, five, six, or any other suitable number of needle receptacles 162 may be formed in the base portion 156 in any suitable configuration.

At least a portion of the base portion 156 may be formed of one or more semi-flexible materials such as polymers, polymeric composites, metals, combinations thereof, or the like. As explained in more detail below, configuring the base portion 156 in this manner may allow the needle removal device 152 to move between a receiving position, wherein at least a portion of each needle 108 can pass through the needle receptacles 162 and the grooves 160, and a grasping position, wherein the grooves 160 grasp or pinch the needles 108 between the opposing side walls of the grooves 160. Such a configuration may allow a user to exert a force in the proximal direction on the needles 108 to overcome an initial resistance to removal of the needles 108 from the guide body 102. For example, in the grasping position, the needle removal device 152 may allow a user to exert a force in the proximal direction of about one quarter (0.25) pound-force to seventy (70) pound-force; about one (1) pound-force to sixty (60) pound-force; or about five (5) pound-force to forty (40) pound-force on the needles 108 to overcome an initial resistance to proximal movement of the needles 108 from the guide body 102. In other embodiments, the needle removal device 152 may allow a user to exert larger or smaller forces on the needles 108. At least a portion of the sidewalls of the grooves 160 may include gripping features such as ridges, textured surfaces, adhesives, magnets, or other features suitable to help grip the needles 108 in the grooves 160. In other embodiments, the gripping features may be omitted.

Figure 1F:
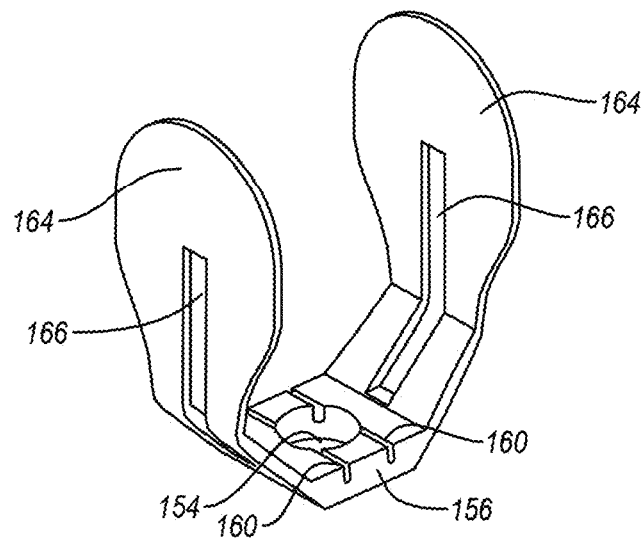
FIG. 1F illustrates a top perspective view of a needle removal device according to another embodiment.

Referring still to FIGS. 1D-1F, the tabs 164 may be configured to move the needle removal device 152 between the receiving and grasping positions. As shown, the tabs 164 may be integral to the base portion 156. In other embodiments, the tabs 164 may be connected to the opposite ends of the base portion 156 via adhesives, threaded attachment, fastening with a fastener, welding, combinations of the foregoing, or another suitable technique. The tabs 164 may be generally elongated rectangles and extend proximally from the base portion 156. The tabs 164 may have a height defined between the top surface of the base portion 156 and a proximal end of the tabs 164. The base portion 156 may have a length defined between the opposite ends of the base portion 156. The height of the tabs 164 may be greater or smaller than the length of the base portion 156. The height of one or more of the tabs 164 may be about thirty (30) percent to one hundred fifty (150) percent; about forty (40) percent to one hundred forty (140) percent; about 50 percent to one hundred thirty (130) percent; about sixty (60) percent to one hundred twenty (120) percent; about seventy (70) percent to one hundred ten (110) percent the length of the base portion 156. In other embodiments, the height of one or more of the tabs 164 may be more or less relative to the length of the base portion 156.

During use of the needle removal device 152, a user may squeeze proximal free end portions of the tabs 164 together to move the needle removal device 152 from the receiving position to the grasping position. This may be done with the user's hand, a tool, or by any other suitable means. The tabs 164 may function as moment arms to flex or bow the base portion 156 of the needle removal device 152. As the tabs 164 flex the base portion 156, the needle removal device 152 may move toward the grasping position, wherein the grooves 160 grasp or pinch the needles 108 between the opposing side walls of the grooves 160. With the needle removal device 152 in the grasping position, the user may release the proximal free end portions of the tabs 164 to allow the tabs 164 to return to a resting position. In the resting position, the base portion 156 may relax and the needle removal device 152 may move back toward the receiving position. As shown, such a configuration of the needle removal device 152 may position the tips of the needles 108 between the tabs 164 such that the risk of injury to a user or patient is reduced.

As shown, the tabs 164 may include a substantially planar inner surface and a substantially concavely curved outer surface. In other embodiments, the inner and/or outer surface of the tabs 164 may be generally planar, contoured, concavely curved, convexly curved, contoured, irregular, or any other suitable configuration. For example, the outer surface of the tabs 164 may include a tool indentation configured to selectively receive a distal portion of a hemostat or other medical instrument. In other embodiments, the outer surface of the tabs 164 may include gripping features configured to help a user squeeze the proximal free end portions of the tabs 164 together. For example, the outer surface of the tabs 164 may include a textured surface configured as a grip for a user's fingers. In other embodiments, the outer surface of the tabs 164 may include ridges, ergonomical indentations, or the like.

While the tabs are as illustrated being generally elongated rectangles, the tabs may be generally oval, generally triangular, generally diamond-like, irregularly shaped, or any other suitable shape. For example, as shown in FIG. 1F, the tabs 164 may be configured similarly to the interlock wings 116. The tabs 164 may include generally trapezoidal distal portions connected to the opposite ends of the base portion 156. The distal portions of the tabs 164 may be angled relative to the base portions 156. The tabs 164 may also have a substantially wing-like proximal free end portion angled relative to the distal portion of the tabs 164. In other embodiments, the tabs 164 may include elongated slots 166 extending therethrough and along an axis of the tabs 164 to generally correspond to a support structure formed on an inner surface of the interlock wings 116. In other embodiments, the elongated slots may be omitted from the tabs 164. For example, the tabs 164, without elongated slots, may be positioned on the suturing system 10 such that the tabs 164 are rotated ninety (90) degrees relative to the interlock wings 116.

FIGS. 2A through 2D illustrate steps for removing needles from the suturing device 10 with the needle removal device 152. While the method is illustrated using the suturing system 10, it will be appreciated that the described method may utilize any other suturing system or system disclosed herein. Moreover, for ease of reference, one of the interlock wings 116 has been removed from the suturing system 10.

Figure 2A:
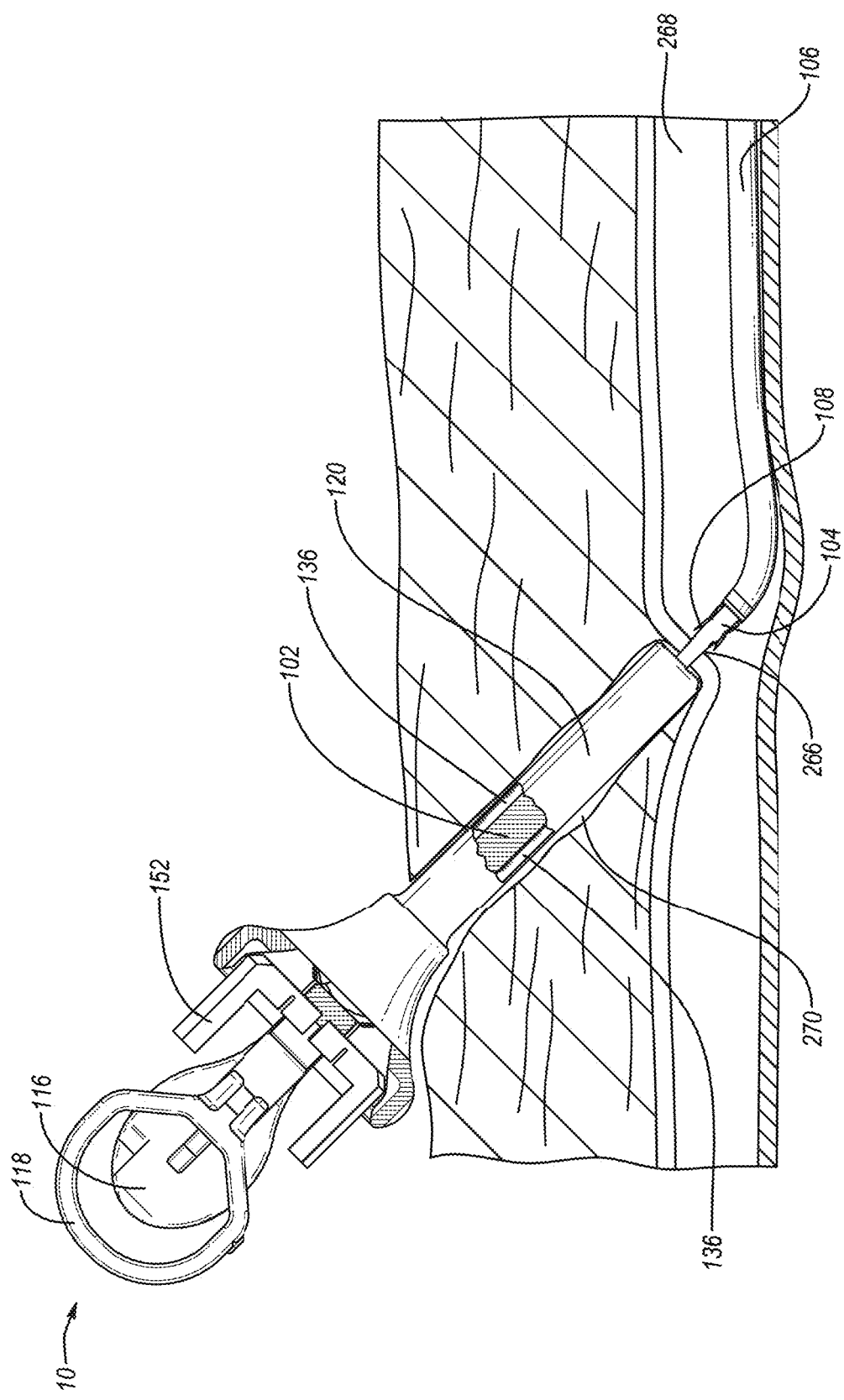
FIGS. 2A-2D illustrate exemplary steps for removing needles from the suturing device shown in FIG. 1A.

Referring now to FIG. 2A, the method can begin by advancing the suturing system 10 through an access tract 270 to position the needles 108 encased by the flexible tube 106 within the vessel 268 past the puncture site 266. In other embodiments, the suturing system 10 may be introduced over a guide wire (not shown) passing through the vessel 268. For example, an introducer sheath (not shown) may be placed over a guide wire passing percutaneously beneath the patient's skin. The introducer sheath may then be withdrawn from the puncture site 266 by sliding the introducer sheath over the guide wire. The suturing system 10 may then be introduced over the guide wire by passing the guide wire proximally through the flexible tube 106 until the guide wire exits the exit port 134 (shown in FIG. 1A). The flexible tube 106 may then be further advanced over the guide wire until the needle guide 104 is about to enter the access tract 270. At this point, the guide wire is pulled from the flexible tube 106 and is withdrawn from the puncture site 266. With the guide wire removed, the suturing system 10 may be further advanced into the vessel 268 to pass the needle guide 104 through the access tract 270 into the vessel 268.

Figure 2B:
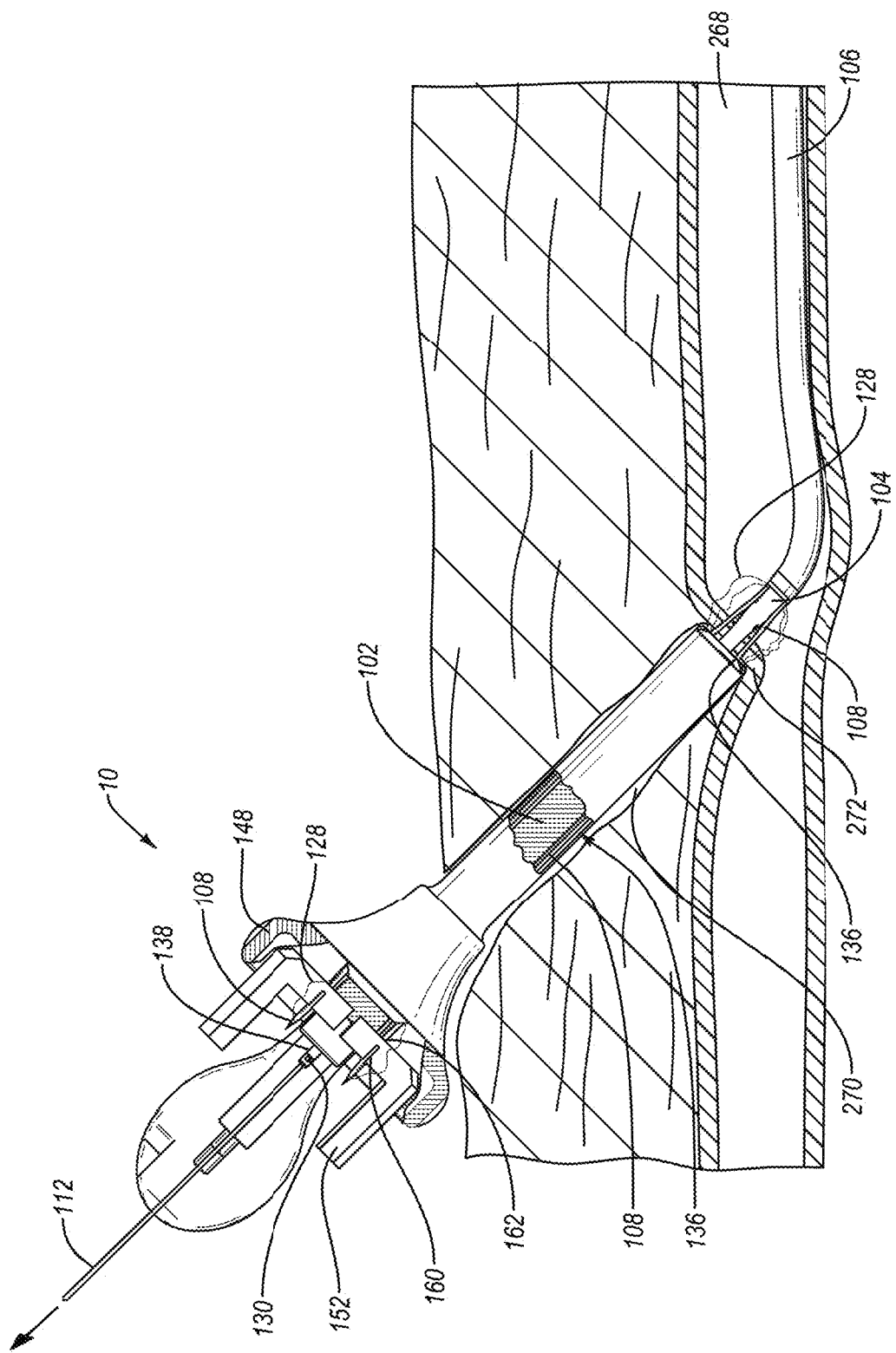

Referring now to FIG. 2B, to deploy the needles 108, the handle 118 (shown in FIG. 2A) may be drawn proximally relative to the guide body 102 to proximally move the needle deployment shaft 112. In other embodiments, the handle 118 may be rotated counter-clockwise to disengage the key from the slot in the stem 138 prior to drawing the handle 118 proximally. As shown, the needles 108 will exit from the needle guide 104, pass through the vessel wall 272, and will be directed toward the needle lumens 136 of the guide body 102. As the needles 108 are drawn through the vessel wall 272, the suture lengths 128 will be fed distally through the one or more suture lumens 126 (shown in FIG. 1C). The needles 108 will then be advanced into the needle lumens 136, with the suture lengths 128 being continually fed through the one or more suture lumens 126. The handle 118 may continue to be drawn proximally (i.e., outward from the patient) in order to continue to pull the needles 108 through the guide body 102. Such movement of the needles 108, in turn, continues to draw the needles 108 proximally through the needle lumens 136 of the guide body 102 until the needles 108, with the suture lengths 128 still attached thereto, exit the hub 148 and are received within the needle receptacles 162 and/or the grooves 160 of the needle removal device 152 as shown in FIG. 2B. At that point, the looped portions of the suture lengths 128 may be removed from the one or more suture lumens 126.

Figure 2C:
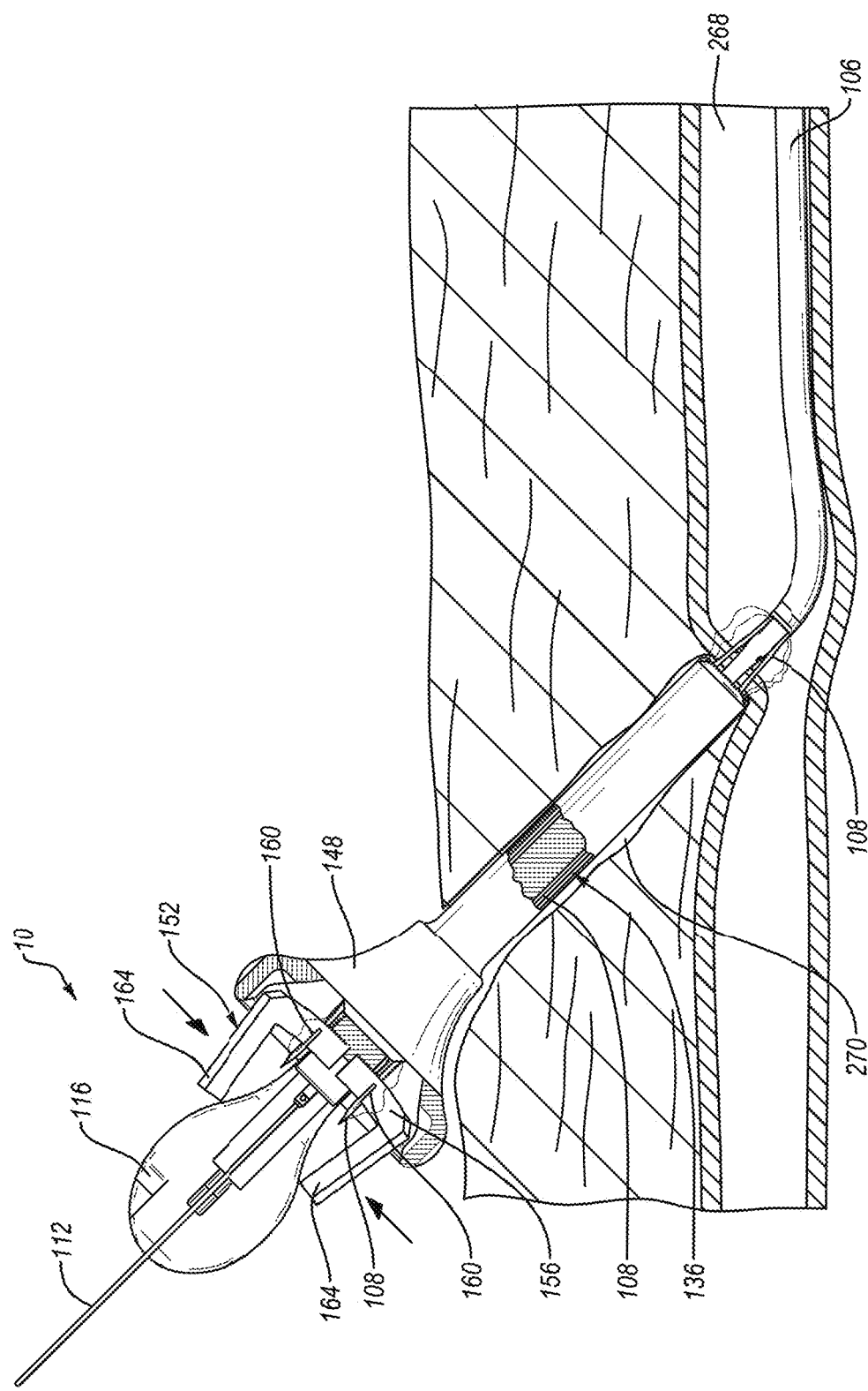

Referring now to FIG. 2C, the proximal free end portions of the tabs 164 may be squeezed or pushed together (i.e., moved to the actuated position) to flex the base portion 156 such that the needle removal device 152 moves to the grasping position. The tabs 164 may be squeezed or pushed together with a user's fingers, a hemostat, or any other suitable means. In the grasping position, the needles 108 may be grasped by the needle removal device 152 between the opposing sidewalls of the grooves 160. In other embodiments, the sidewalls of the grooves 160 may include gripping features configured to help grasp the needles 108 such as ridges, textured surfaces, magnets, or other suitable means.

Figure 2D:
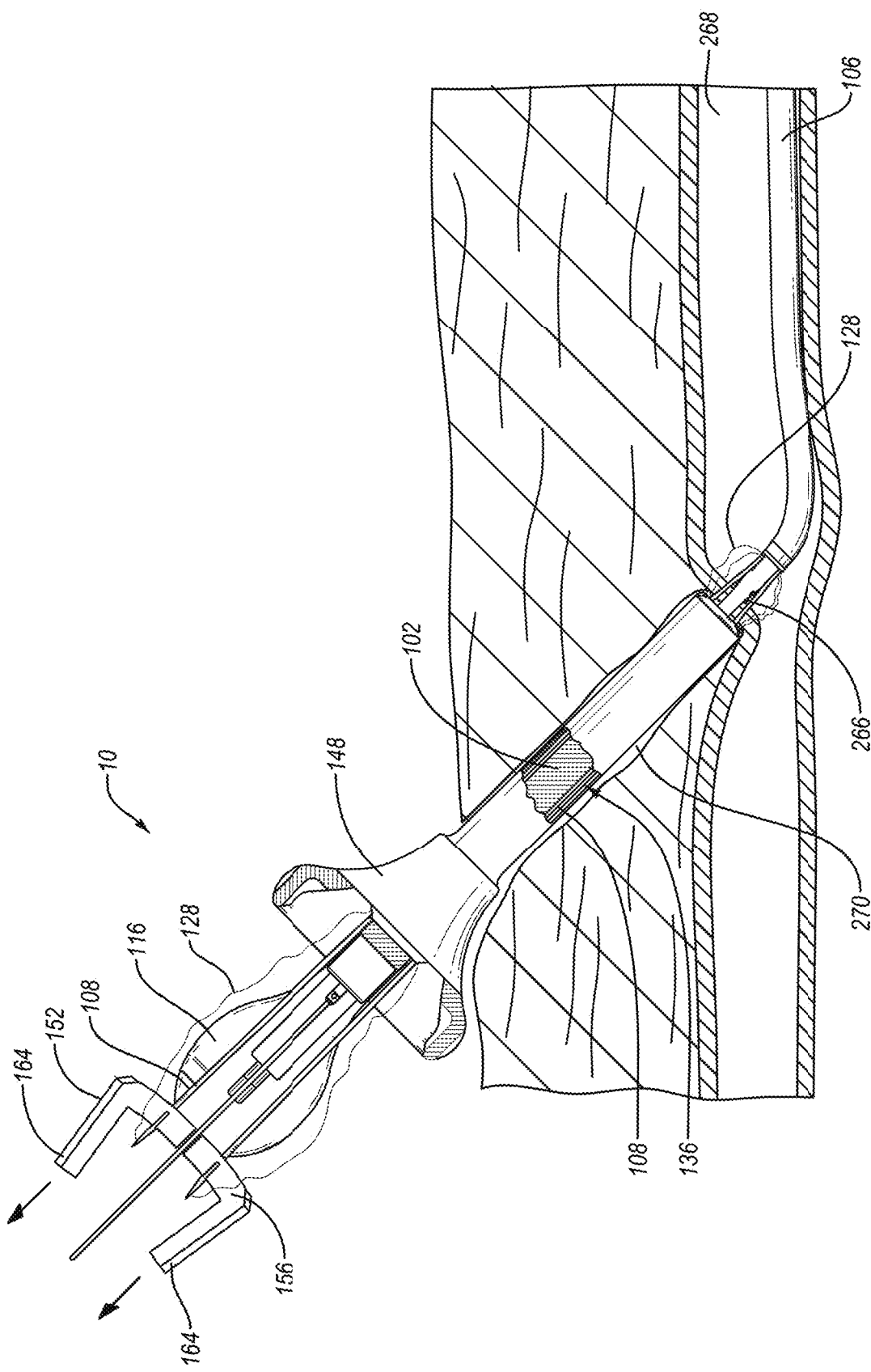

Referring now to FIG. 2D, with the needle removal device 152 in the grasping position, the needle removal device 152 may be moved proximally relative to the guide body 102. Proximal movement of the needle removal device 152, in turn, may continue to remove the needles 108 from the guide body 102 until the suture lengths 128 are available to the user. Once the needles 108 are removed from the guide body 102, slack may be removed from the suture lengths 128 by pulling them to evenly matched lengths and tensioning until resistance is felt. The suture lengths 128 may then be cut substantially close to the needles 108 and the needles 108 may be disposed of. The suturing system 10 may then be removed from the access tract 270 to allow closure of the puncture site 266. Such a configuration of the suturing system 10 may allow a user to safely and securely close a puncture site.

In other embodiments, the suturing system 10 may be readily adapted for use with punctures made to a variety of hollow body organs and lumens. It may, however, be necessary to modify the dimensions and other particular aspects of the suturing system 10 to accommodate the different usage environments. For example, the distance between the needle guide 104 and the guide body 102 may be configured to allow transapical insertion of the suturing system 10 into a heart ventricle as described in U.S. Patent Application, entitled "Apparatus and Method for Suturing Body Lumens," Ser. No. 13/443,659, the disclosure of which is incorporated herein in its entirety.

Another embodiment of a needle removal device will now be described in relation to FIGS. 3A through 4B. A suturing system 30 may be similar in many respects to the suturing system 10 previously described above in FIGS. 1A-2D. To the extent features or components of this configuration function in a manner similar to that as described above, such disclosure is hereby incorporated into the following additional configuration. Like structures and/or components are given like reference numerals. For ease of reference, only the proximal portion of the suturing system 30 is shown and described. The distal components may be manipulated by the proximal components in a similar manner as described with references to FIGS. 1A through 2D.

Figure 3A:
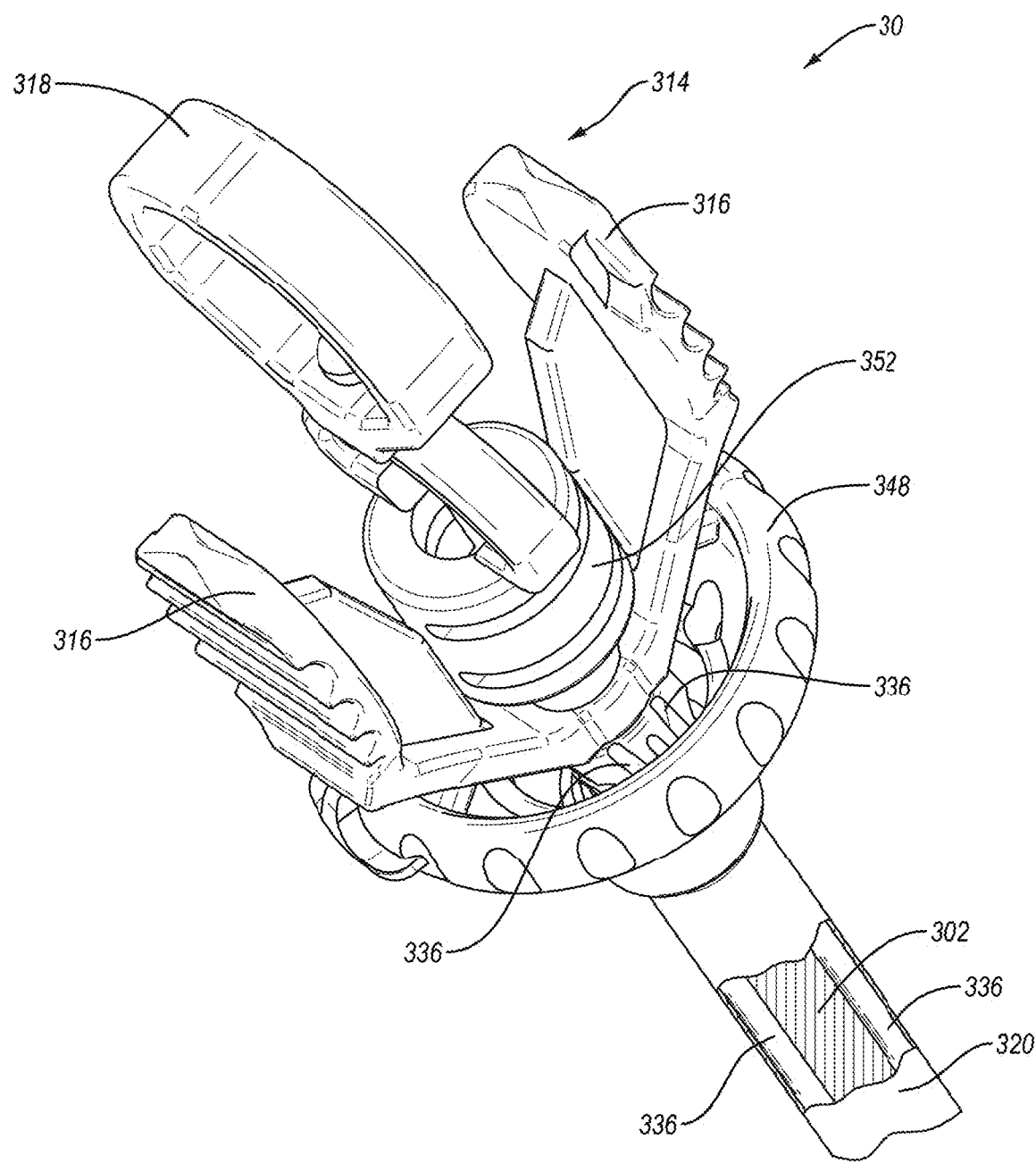
FIG. 3A illustrates a partial side perspective view of a suturing system according to another embodiment.

FIG. 3A is a partial side perspective view of the suturing system 30. The suturing system 30 may include a guide body 302, a needle guide (not shown) secured to a distal end of the guide body 302, and a flexible tube (not shown) secured to a distal end of the needle guide. A sheath 320 may be rotatably received over the guide body 302. A plurality of needles 308 (shown in FIG. 4A) may be mounted with their distal ends in a support holster (not shown) and attached to a movable needle deployment shaft 312 (shown in FIG. 4A). A handle assembly 314 may be attached to a proximal end of the guide body 302. The handle assembly 314 may include a pair of interlock wings 316, a needle removal device 352, and a handle 318. The handle 318 may be attached to a proximal end of the needle deployment shaft 312 and may be pulled proximally in order to draw the needles 308 from the flexible tube, through the needle guide and into the guide body 302 until the tips of the needles 308 emerge from the guide body 302 within a hub 348 of the sheath 320. Once the needles 308 emerge within the hub 348, the needles 308 may be received by the needle removal device 352.

Figure 3B:
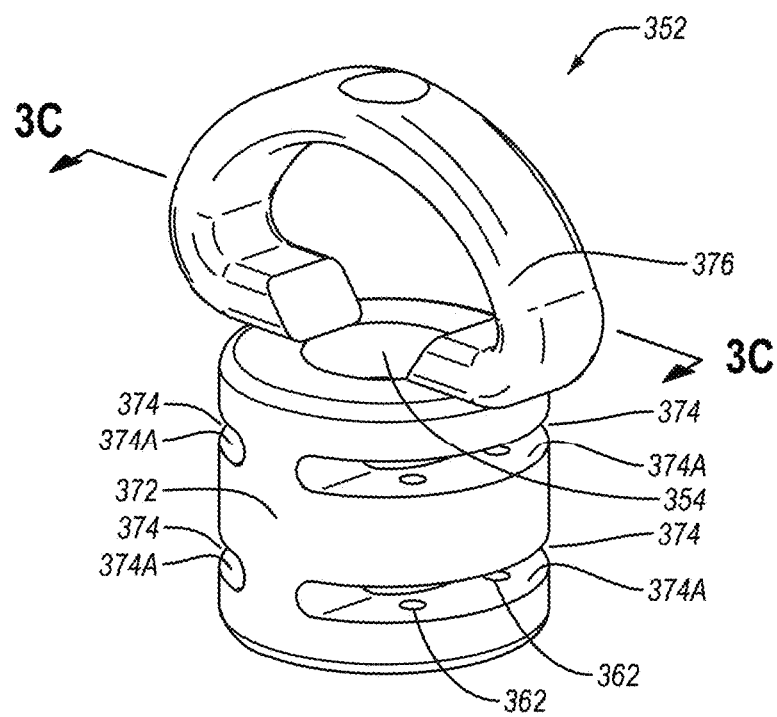
FIG. 3B illustrates a perspective view of the needle removal device removed from the suturing system shown in FIG. 3A.

FIG. 3B is an isometric view of the needle removal device 352 removed from the suturing system 30. As shown, the needle removal device 352 may include a generally cylindrical body 372 and a handle portion 376. The needle removal device 352 may be made from polymers, polymeric composites, titanium, stainless steel, metal alloys, combinations thereof, or any other suitable materials.

The body 372 may include a central aperture 354 extending therethrough configured to allow a stem 338 (shown in FIG. 4B) of the handle assembly 314 to pass through the body 372. The central aperture 354 may also be configured to receive the needle deployment shaft 312 such that the needle deployment shaft 312 may selectively be drawn through the aperture 354 of the needle removal device 352. Accordingly, the needle deployment shaft 312 and the needle removal device 352 may be configured to move axially relative to one another. The needle removal device 352 may be positioned at least partially within the sheath hub 348. In other embodiments, the needle removal device 352 may be positioned proximal the sheath hub 348 or substantially within the sheath hub 348.

The body 372 may include a plurality of needle receptacles 362 formed in a bottom surface of the body 372. The needle receptacles 362 may at least partially define lumens extending through the bottom surface of the body 372 toward an upper surface of the body 372. The lumen of the needle receptacles 362 may have a circular, oval, triangular, or other suitable cross-sectional geometric shape. The lumens of one or more of the needle receptacles 362 may have a constant diameter or a varying diameter. The needle receptacles 362 may be configured and positioned in the body 372 to generally correspond to needle lumens 336 (shown in FIG. 3A) exiting the proximal end of the guide body 302. Such a configuration may allow the needles 308 to be selectively received within the needle receptacles 362 when the needles 308 exit the guide body 302 through the needle lumens 336. As shown, four needle receptacles 362 may be formed in the body 372 about the central aperture 354. In other embodiments, three, five, six, or any other suitable numbers of needle receptacles 362 may be formed in the body 372 in any suitable configuration.

As shown in FIG. 3B, the body 372 may include a plurality of slots 374 formed in a side surface of the body 372. The slots 374 may traverse one or more of the needle receptacles and form a locking edge 374A configured to lock the needles 308 in the needle receptacles 362. As shown, the body 372 may include two pairs of opposing slots 374. In other embodiments, the body 372 may include one, two, three, five, or any other number of slots configured in any suitable configuration. In other embodiments, one or more of the slots 374 may be filled with securing materials such as adhesives, epoxy, or other securing materials configured to help lock the needles 308 in the needle receptacles 362. In other embodiments, the securing materials may be omitted.

Referring still to FIG. 3B, the handle portion 376 may be attached to the upper surface of the body 372. The handle portion 376 may be configured to provide a user a grip to manipulate the needle removal device 352. The handle portion 376 may be integral to the body 372 or the handle portion 376 may be attached to the body 372 via adhesives, threadedly attaching, fastening with a fastener, welding, combinations of the foregoing, or another suitable technique. The central aperture 354 may also extend through the handle portion 376 such that the needle deployment shaft 312 may pass through the handle portion 376.

In other embodiments, the handle portion 376 may be configured to rotate relative to the body 372 such that the needle removal device 352 may be selectively locked on the stem 338. For example, the handle portion 376 may include a shaft portion (not shown) attached thereto that extends through the central aperture 354 between the stem 338 and the body 372. The shaft portion may include a rib feature at a distal end configured to maintain the shaft portion within the body 372. In other embodiments, the shaft portion may include a key (not shown) that is received within a slot (not shown) in the stem 338. Such a configuration may allow the needle removal device 352 to be slid over the stem 338 with the key being received in the slot. The handle portion 376 of the needle removal device 352 may be rotated in a clockwise direction to rotate the shaft portion to secure the needle removal device 352 to the stem 338 in order to prevent axial movement of the needle removal device 352. To move the needle removal device 352 axially, the handle portion 376 of the needle removal device 352 may be rotated in a counterclockwise direction so that the key may be pulled from the slot. The needle removal device 352 may then be moved proximally. In other embodiments, the handle portion 376 and the shaft portion may be omitted from the needle removal device 352.

Figure 3C:
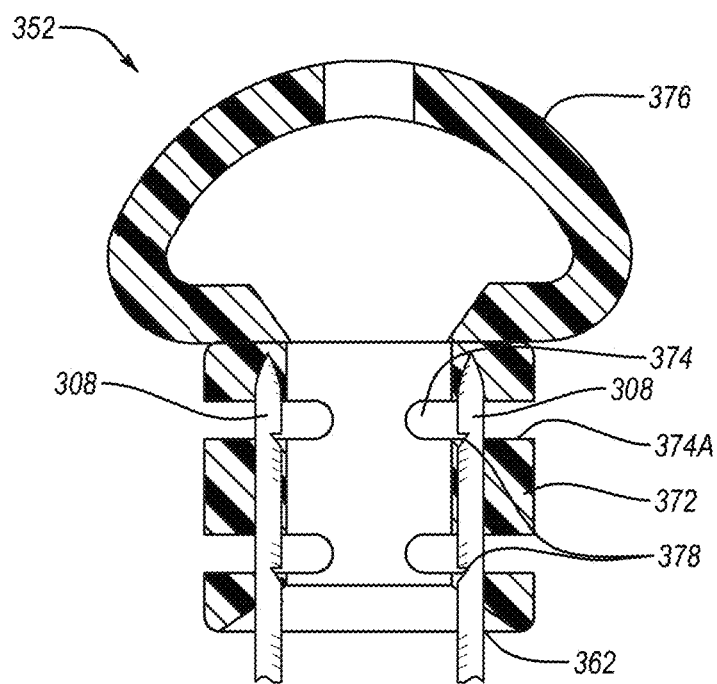
FIG. 3C illustrates a cross-sectional view of the needle removal device shown in FIG. 3B taken along line 3C-3C.

FIG. 3C is a cross sectional view of the needle removal device 352 with the needles 308 inserted in the needle receptacles 362. As shown, the needles 308 may include notches 378 formed in a shaft portion of the needles 308. The notches 378 may be formed circumferentially about the shaft portion, on one side of the shaft portion, or in any other part of the shaft portion of the needles 308. The notches 378 may be configured to selectively lock on the locking edge 374A of the slots. For example, once the needles 308 are received within the needle receptacles 362, the locking edges may engage the notches 378 of the needles 308. Once engaged, the needles 308 are locked in the needle receptacles 362. Such a configuration may allow a user to remove the needles 308 from the guide body 302.

Referring still to FIG. 3C, the needle receptacles 362 may have a proximal end located within a solid portion of the body 372 such that the tips of the needles 308 may be housed within the body 372 to safeguard against accidental sticks.

Figure 4B:
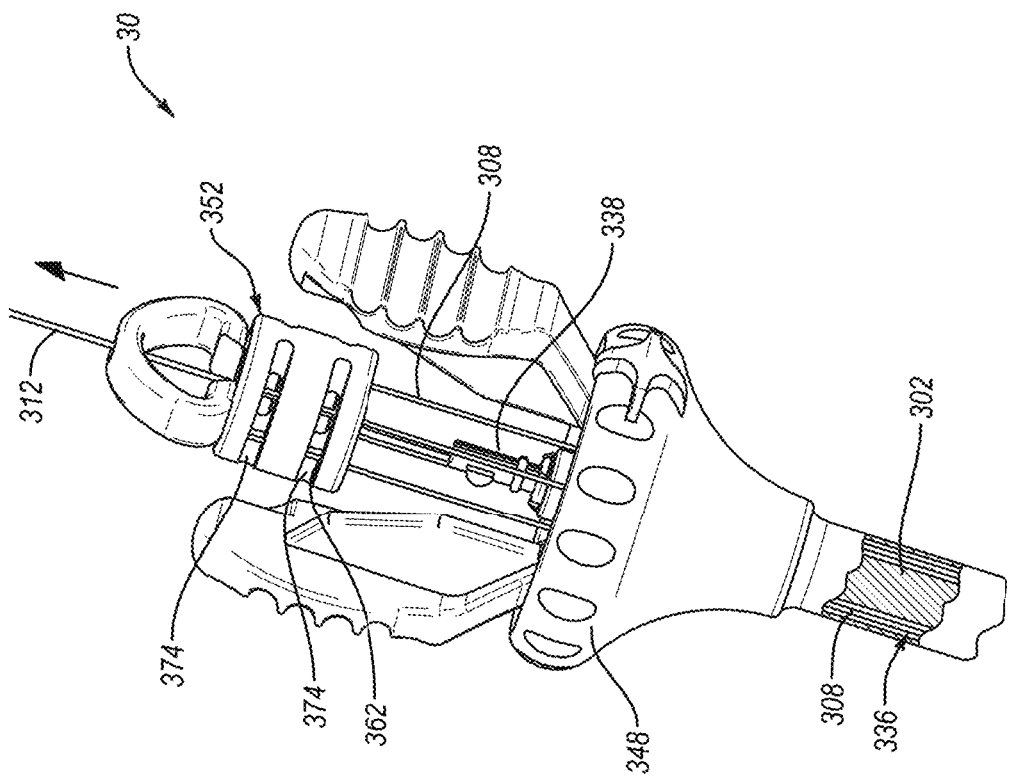
FIGS. 4A-4B illustrate exemplary steps for removing needles from the suturing system shown in FIG. 3A.
Figure 4A:
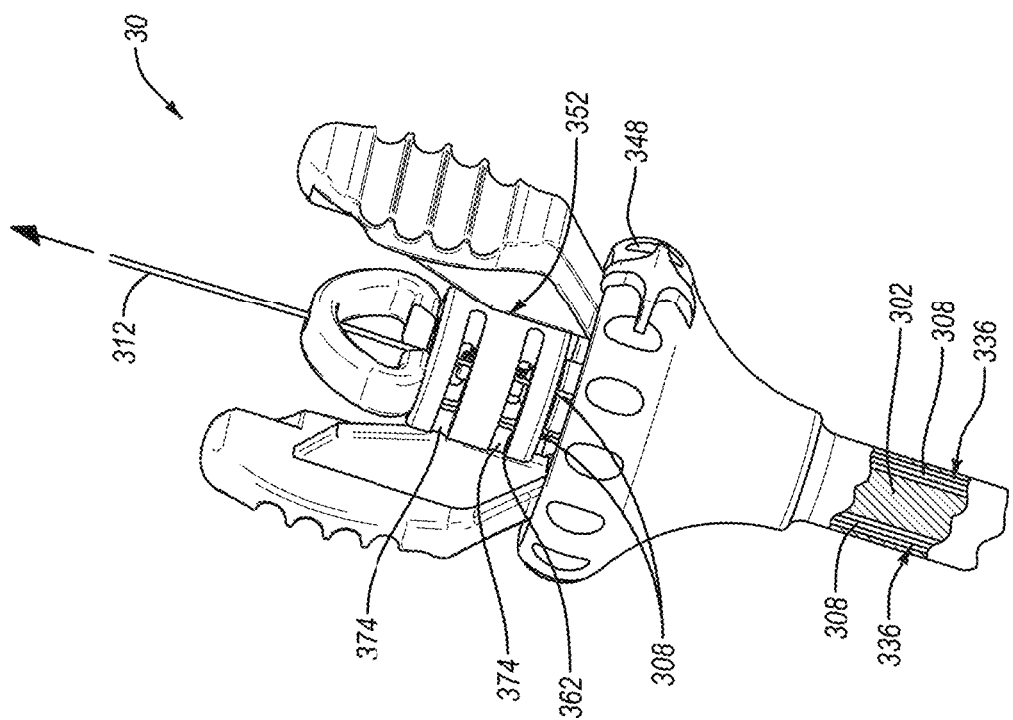

FIGS. 4A and 4B illustrate exemplary steps in a method for removing the needles 308 from the suturing system 30 with the needle removal device 352. While the method is illustrated using the suturing system 30 and the needle removal device 352, it will be appreciated that the described method may utilize any other needle removal device and/or suturing system disclosed herein. Only certain exemplary steps of removing the needles 308 from the suturing system 30 are shown and described, however, it will be appreciated that the method may follow delivery of needles and suture lengths through body tissue or a vessel wall by the suturing system 30. For example, the method may include any of the steps previously described and/or illustrated in relation to FIGS. 2A through 2E.

Referring now to FIG. 4A, to deploy the needles 308, the handle 318 (shown in FIG. 3A) may be drawn proximally relative to the guide body 302 to proximally move the needle deployment shaft 312. As shown, the needle deployment shaft 312 may draw the needles 308 proximally through the needle lumens 336 of the guide body 302 until the needles 308 exit the guide body 302 within the hub 348. As the needles 308 exit the guide body 302, they may be received within the needle receptacles 362 of the needle removal device 352 as shown. Once the needles 308 are received within the needle receptacles 362, the locking edges of the slots 374 may engage the notches 378 (shown in FIG. 3C) in the needles 308. Such a configuration may substantially lock the needles 308 in the needle receptacles 362. As shown, the tips of the needles 308 may be safely housed in the solid portion of the body 372 such that risk of injury to a user or patient from the tips of the needles 308 is reduced.

Referring now to FIG. 4B, with the needles 308 locked in the needle receptacles 362, the needle removal device 352 may be drawn proximally to pull the needles 308 out of the guide body 302. Once the needles 308 are removed from the guide body 302, suture lengths (not shown) attached to the needles 308 may be cut and the needles 308 may be disposed of. Such a configuration of the needle removal device 352 may allow a user to safely and quickly remove the needles 308 from the suturing system 30.

Another embodiment of a needle removal device will now be described in relation to FIGS. 5A through 6C. A suturing system 50 may be similar in many respects to the suturing system 10 and the suturing system 30 previously described above in FIGS. 1A-4B. To the extent features or components of this configuration function in a manner similar to that as described above, such disclosure is hereby incorporated into the following additional configuration. Like structures and/or components are given like reference numerals. Similar to suturing system 30, for ease of reference, only the proximal portion of the suturing system 50 is shown and described. The distal components may be manipulated by the proximal components in a similar manner as described with reference to FIGS. 1A through 2D.

Figure 5A:
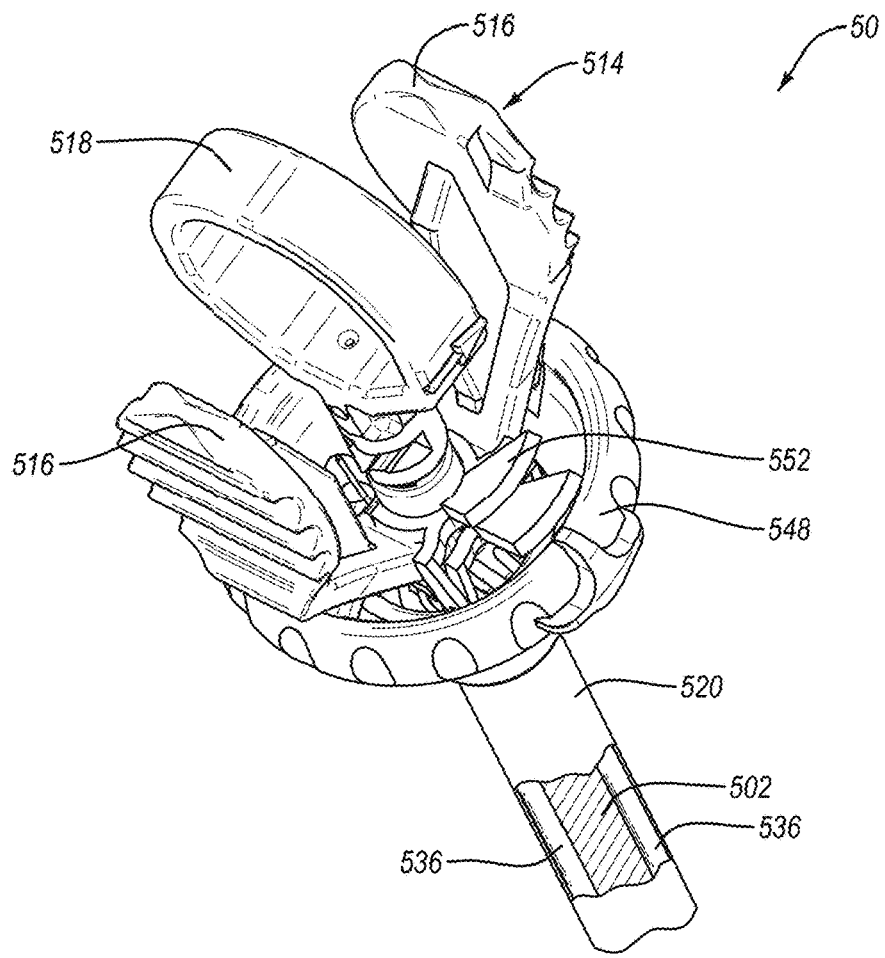
FIG. 5A is a partial side perspective view of a suturing system according to another embodiment.

FIG. 5A is a partial side perspective view of the suturing system 50. The suturing system 50 may include a guide body 502, a needle guide (not shown) secured to a distal end of the guide body 502, and a flexible tube (not shown) secured to a distal end of the needle guide. A sheath 520 may be rotatably received over the guide body 502. A plurality of needles 508 (shown in FIG. 6A) may be mounted with their distal ends in a support holster (not shown) and attached to a movable needle deployment shaft 512 (shown in FIG. 6A). A handle assembly 514 may be attached to a proximal end of the guide body 502. The handle assembly 514 may include a pair of interlock wings 516, a needle removal device 552, and a handle 518. The handle 518 may be attached to a proximal end of the needle deployment shaft 512 and may be pulled proximally in order to draw the needles 508 from the flexible tube, through the needle guide and into the guide body 502 until the needles 508 emerge from the guide body 502 within a hub 548. Once the needles 508 emerge within the hub 548, the needles 508 may be received within the needle removal device 552. While one needle removal device 552 is shown, the suturing system 50 may include two, three, or any suitable number of needle removal devices 552. For example, the suturing system 50 may include two needle removal devices 552 located on opposites sides of the guide body 502 such that a total of four needles may be received within the needle removal devices 552 on the opposite sides of the guide body 502.

Figure 5B:
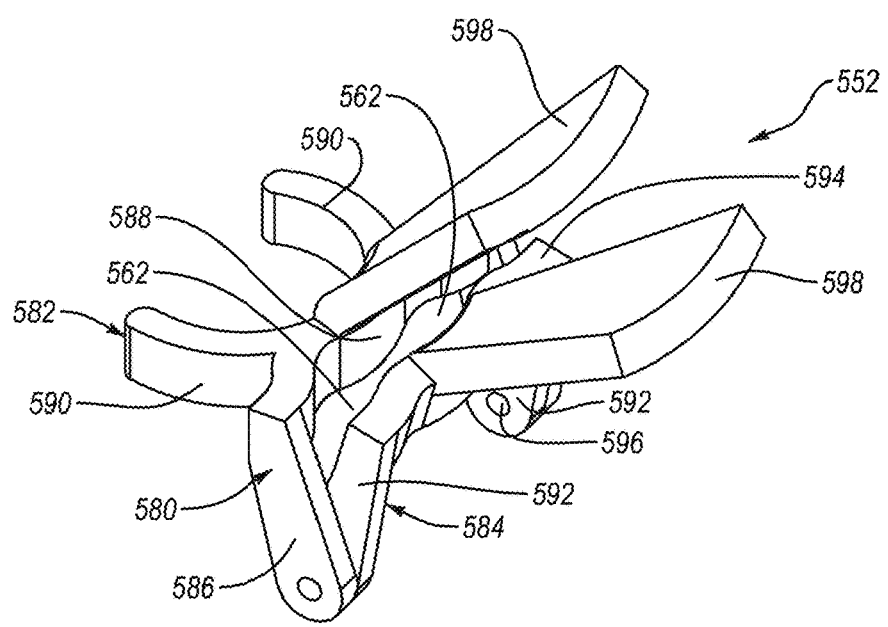
FIG. 5B is a perspective view of the needle removal device removed from the suturing system shown in FIG. 5A.

FIG. 5B is an isometric view of the needle removal device 552 removed from the suturing system 50. As shown, the needle removal device 552 may include a base member 580, an attachment ring 582, and a pivoting member 584. The needle removal device 552 may be formed from polymers, polymeric composites, titanium, stainless steel, combinations thereof, or any other suitable materials.

The base member 580 may include a pair of base support arms 586 and a base cross member 588. The base support arms 586 may have proximal portions attached to opposite ends of the base cross member 588 and the attachment ring 582. In other embodiments, the base support arms 586 may be attached to the guide body 502, the hub 548, or any other suitable part of the suturing system 50. As shown, the attachment ring 582 may include a pair of attachment arms 590 configured to selectively attach the needle removal device 552 to a stem 538 (shown in FIG. 6A) proximal to the guide body 502. As shown, the attachment arms 590 may form at least a portion of circle having a diameter configured to generally correspond to an outer diameter of the stem 538.

The attachment arms 590 may be configured to flex apart such that the attachment ring 582 may be removably attached to the stem 538 by moving the attachment ring 582 in a direction substantially traverse to the stem 538. In other embodiments, the attachment arms 590 may be resiliently biased, substantially rigid, or they may have any other configuration suitable to attach and remove the attachment ring 582 from the stem 538.

Similar to the base member 580, the pivoting member 584 may include a pair of pivoting support arms 592 and a pivoting cross member 594. The pivoting support arms 592 may have proximal portions attached to opposite ends of the pivoting cross member 594 and distal portions pivotally connected to distal portions of the base support arms 586. The pivoting support arms 592 may pivot about one or more pivot pins 596 inserted through one or more apertures extending through the distal portions of the pivoting support arms 592 and the base support arms 586. In other embodiments, the pivoting support arms 592 may be pivotally connected to the base support arms 586 via a ball and joint type connection, a pivoting hinge connection, or any other suitable pivoting connection.

The needle removal device 552 may be moveable between a receiving position, wherein the base member 580 and the pivoting member 584 are moved apart such that needles 508 (shown in FIG. 6A) may extend therebetween, and a grasping position, wherein the base member 580 and the pivoting member 584 are moved together to the grasp or pinch needles 508 between the base member 580 and the pivoting member 584.

As shown, the needle removal device 552 may include one or more needle receptacles 562 configured to receive the needles 508. The one or more needle receptacles 562 may be defined at least partially as the region between the pivoting cross member 594 and the base cross member 588. The one or more needle receptacles 562 may be configured and positioned to generally correspond to needle lumens 536 at the proximal end of the guide body 502. Such a configuration may allow the needles 508 to be received within the needle receptacles 562 when the needles 508 exit the needle lumens 536. The one or more needle receptacles 562 may include grasping portions formed between the pivot cross member 594 and the base cross member 588. In other embodiments, the grasping portions may include one or more gripping features such as ridges, textured surfaces, contoured surfaces, adhesive, magnets, or other features suitable to enhance the grip of the needle removal device 552 on the needles 508. In addition, the base member 580 and/or the pivoting member 584 may be substantially rigid to improve compliance of the needle removal device 552 and to enhance the grip of the needle removal device 552 on the needles 508. Such a configuration may allow a user to exert a force in the proximal direction on the needles 508 to overcome an initial resistance to removal of the needles 508 from the guide body 502. For example, in the grasping position, the needle removal device 552 may allow a user to exert a force in the proximal direction of about one quarter (0.25) pound-force to seventy (70) pound-force; about one (1) pound-force to sixty (60) pound-force; or about five (5) pound-force to forty (40) pound-force on the needles 508. In other embodiments, the needle removal device 552 may allow a user to exert larger or smaller forces on the needles 508.

The needle removal device 552 may include a pair of tabs 598. The tabs 598 may be connected to the base cross member 588 and the pivoting cross member 594, respectively. The tabs 598 may be integral to the cross members 588, 594 or the tabs 598 may be connected to the cross members 588, 594 via adhesives, threadedly attaching, fastening with a fastener, welding, combinations of the foregoing, or another suitable technique. The tabs 598 may be configured to allow a user to move the needle removal device 552 between the receiving and grasping positions. For example, a user may push or squeeze the tabs 598 together to move the needle removal device 552 toward the grasping position. The user may push or squeeze the tabs 598 together with a user's fingers, a hemostat, or other suitable means.

The needle removal device 552 may include locking features configured to selectively lock the needle removal device 552 in the grasping position. For example, one of the tabs 598 may include one or more locking arms configured to rotate over the other tab 598 when the needle removal device 552 is in the grasping position to hold the tabs 598 together. The other tab 598 may include one or more grooves configured to receive and/or secure the one or more locking arms on the other tab 598. In other embodiments, the locking features may include a hook member configured to hold the tabs 598 together in the grasping position. In other embodiments, the locking features may be omitted.

Figure 6C:
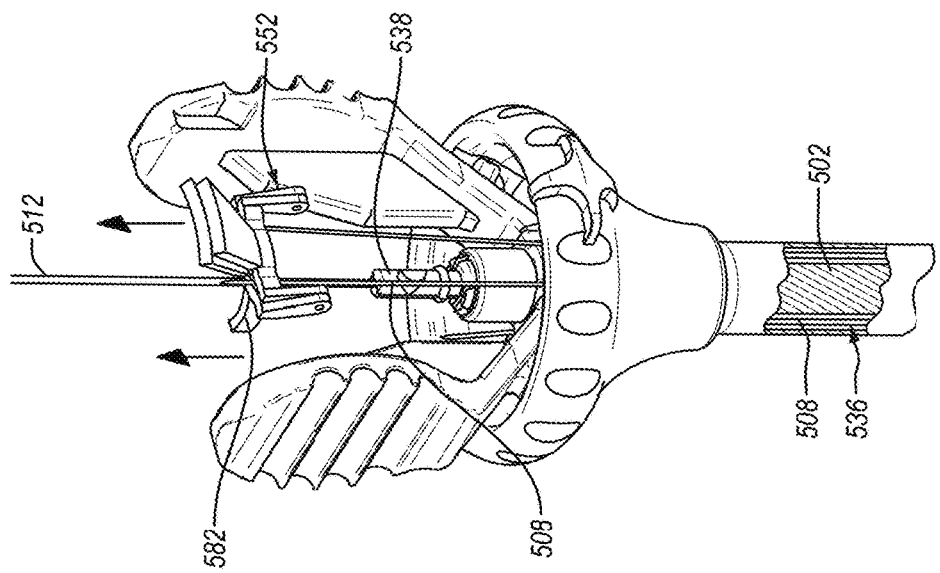
FIGS. 6A-6C illustrate exemplary steps for removing needles from the suturing system shown in FIG. 5A with the needle removal device.
Figure 6B:
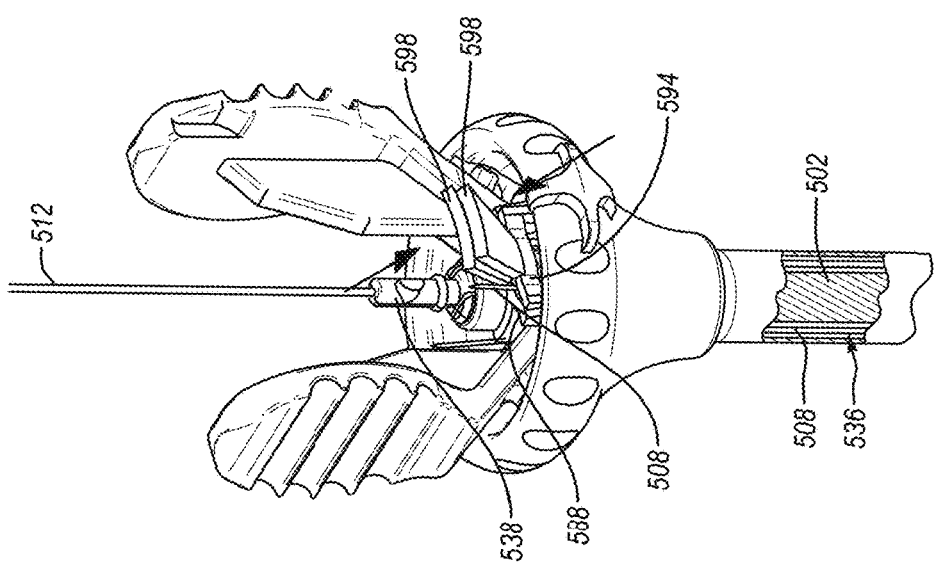
Figure 6A:
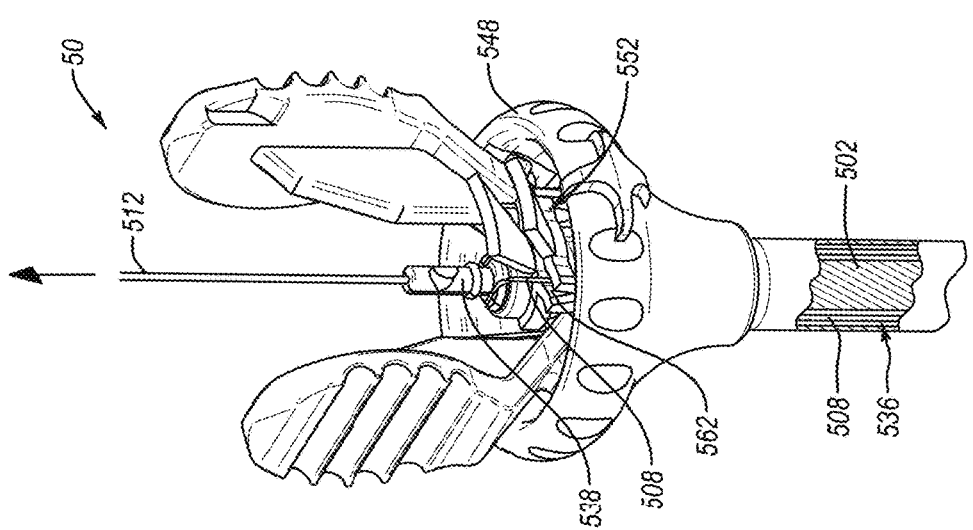

FIGS. 6A through 6C illustrate exemplary steps in a method for removing the needles 508 from the suturing system 50 with the needle removal device 552. While the method is illustrated using the suturing system 50 and the needle removal device 552, it will be appreciated that the described method may utilize any other needle removal device and/or suturing system disclosed herein. Only certain exemplary steps of removing the needles 508 from the suturing system 50 are shown and described, however, it will be appreciated that the method may follow delivery of needles and suture lengths through body tissue or a vessel wall by the suturing system 50. For example, the method may include any of the steps previously described and/or illustrated in relation to FIGS. 2A through 2D.

Referring now to FIG. 6A, to deploy the needles 508, the handle 518 (shown in FIG. 5A) may be drawn proximally relative to the guide body 502 to proximally move the needle deployment shaft 512. As shown, the needle deployment shaft 512 may draw the needles 508 proximally through the needle lumens 536 of the guide body 502 until the needles 508 exit the guide body 502 within the hub 548. As the needles 508 exit the guide body 502, the needles 508 may be received within the needle receptacles 562 while the needle removal device 552 is in the receiving position as shown.

Referring now to FIG. 6B, the tabs 598 may be squeezed or pushed together to move the needle removal element 552 into the grasping position. The tabs 598 may be squeezed or pushed together with a user's fingers, a hemostat, or any other suitable means. In the grasping position, the needles 508 may be grasped or pinched by the needle removal device 552 between the pivoting cross member 594 and the base cross member 588 in the grasping portions. The grasping portions may include gripping features configured to help grasp the needles 508 such as adhesives, ridges, textured surfaces, magnets, or other suitable means.

Referring now to FIG. 6C, with the needle removal device 552 in the grasping position, the needle removal device 552 may be moved proximally relative to the guide body 502. The attachment ring 582 may be removed from the stem 538 by moving the attachment ring 582 axially or substantially traverse relative to the stem 538. Proximal movement of the needle removal device 552, in turn, may continue to remove the needles 508 from the guide body 502. Once the needles 508 are removed from the guide body 502, suture lengths (not shown) attached to the needles 508 may be cut and the needles 508 may be disposed of.

Such a configuration of the needle removal device 552 may allow a user to safely and efficiently remove the needles 508 from the suturing system 50.

Another embodiment of a needle removal device will now be described in relation to FIGS. 7A through 8C. A suturing system 70 may be similar in many respects to the suturing systems 10, 30, and 50 previously described above in FIGS. 1A-6C. To the extent features or components of this configuration function in a manner similar to that as described above, such disclosure is hereby incorporated into the following additional configuration. Like structures and/or components are given like reference numerals. Similar to suturing systems 30 and 50, for ease of reference, only the proximal portion of the suturing system 70 is shown and described. The distal components may be manipulated by the proximal components in a similar manner as described with reference to FIGS. 1A through 2D.

Figure 7A:
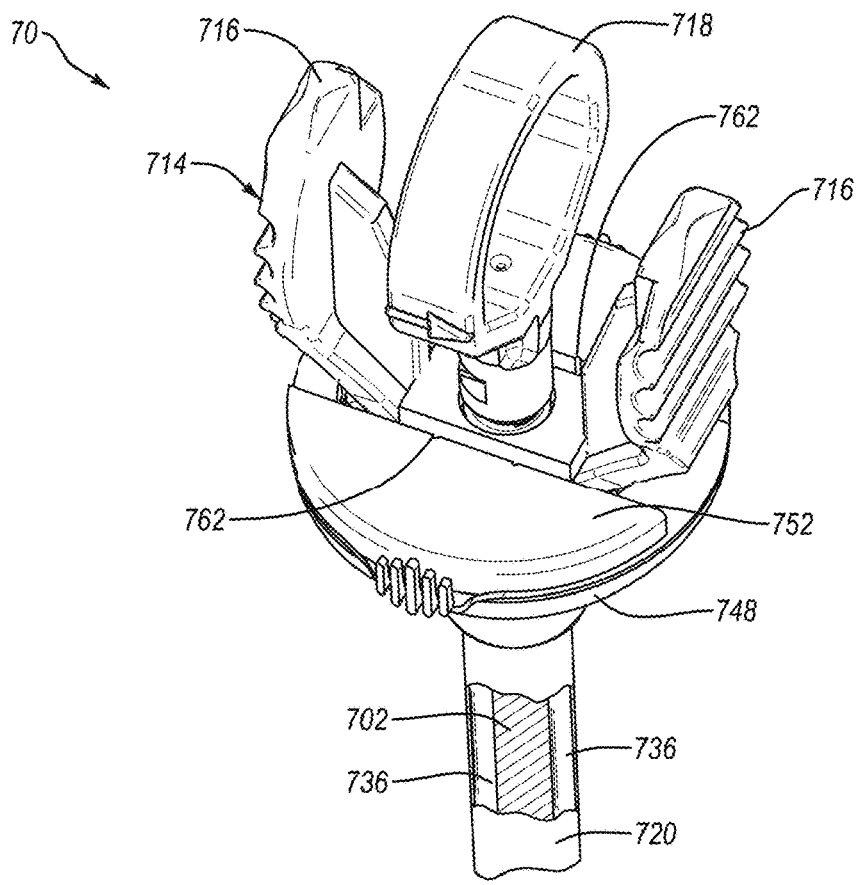
FIG. 7A is a partial side perspective view of a suturing system according to another embodiment.

FIG. 7A is a partial side perspective view of the suturing system 70. The suturing system 70 may include a guide body 702, a needle guide (not shown) secured to a distal end of the guide body 702, and a flexible tube (not shown) secured to a distal end of the needle guide. A sheath 720 may be rotatably received over the guide body 702. A plurality of needles 708 (shown in FIG. 8A) may be mounted with their distal ends in a support holster (not shown) and attached to a moveable needle deployment shaft 712 (shown in FIG. 8A). A handle assembly 714 may be attached to a proximal end of the guide body 702. The handle assembly 714 may include a pair of interlock wings 716, a needle removal device 752, and a handle 718. The handle 718 may be attached to a proximal end of the needle deployment shaft 712 and may be pulled proximally in order to draw the needles 708 from the flexible tube, through the needle guide and into the guide body 702 until the needles 708 emerge from the guide body 702 within a hub 748. Once the needles 708 emerge within the hub 748, the needles 708 may be received within the needle removal device 752. The needle removal device 752 may be location proximal to the hub 748. In another embodiment, the needle removal device 752 may include a lower surface configured to substantially mate with an upper surface of the hub 748 (best shown in FIGS. 8A and 8B).

Figure 7B:
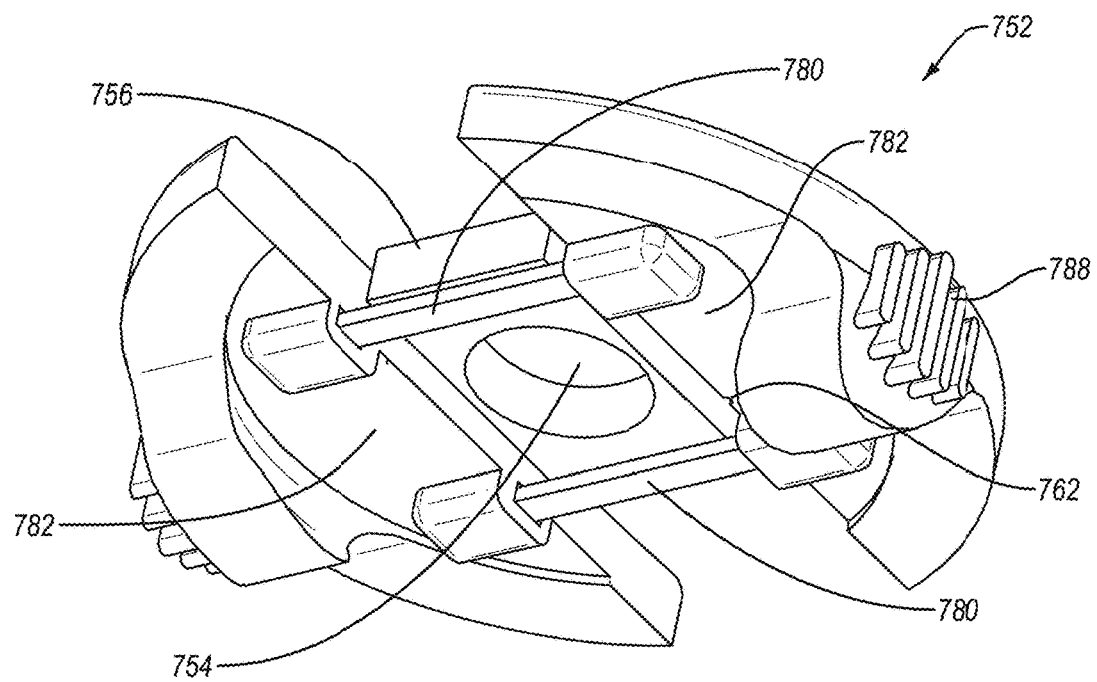
FIG. 7B is a perspective view of the needle removal device removed from the suturing system shown in FIG. 7A.

FIG. 7B is an isometric view of the needle removal device 752 removed from the suturing system 70. As shown, the needle removal device 752 may include a base member 756, guide members 780 connected to the base member 756, and a pair of sliding members 782 slidably positioned on the guide members 780. The needle removal device 752 may be made from polymers, polymeric composites, metals, combinations thereof, or any other suitable material.

The base member 756 may include a central aperture 754 extending therethrough. The central aperture 754 may be configured to allow a stem 738 (shown in FIG. 8A) of the handle assembly 714 to pass through the base member 756 such that the needle removal device 752 may be selectively positioned between the guide body 702 and the handle 718. The central aperture 754 may also be configured to receive the needle deployment shaft 712 such that the needle deployment shaft 712 may be selectively drawn through the base member 756 of the needle removal device 752. Such a configuration may allow the needle deployment shaft 712 and the needle removal device 752 to move axially relative to one another. The base member 756 may have a thickness similar to a thickness of the sliding members 782. In other embodiments, the base member 756 may have a thickness more or less than the thickness of the sliding members 782.

Each of the guide members 780 may be attached to a bottom surface of the base member 756. In other embodiments, the guide members 780 may be attached to and extend from side surfaces of the base member 756. As shown, the guide members 780 may be disposed generally traverse the bottom surface of the base member 756.

Each of the sliding members 782 may be slidably positioned on one or more of the guide members 780 such that the sliding member 782 may move toward and away from the base member 756. The sliding members 782 may have a generally semi-cylindrical geometric shape, a generally semi-oval geometric shape, a generally rectangular geometric shape, a generally triangular geometric shape or any other suitable geometric shape. The sliding members 782 may also include gripping portions 788 on a portion of the periphery of the sliding members 782 configured to provide a user with a grip to manipulate the sliding members 782.

The needle removal element 752 may be moveable between a receiving position, wherein the sliding members 782 and the base member 756 are slid apart such that needles 708 (shown in FIG. 8A) may extend therebetween, and a grasping position, wherein the sliding members 782 and the base member 756 are slid together to grasp or pinch needles 708 between the sliding members 782 and the base member 756. In other embodiments, the guide members 780 may include one or more resilient members (not shown) configured to bias the needle removal element 752 toward the receiving position. Such a configuration may allow a user to squeeze or push the sliding members 782 toward each other along the guide members 780 to move the needle removal element 752 toward the grasping position. The user may push or squeeze the sliding members 782 together with a user's fingers, a medical instrument, or other suitable means. To return the needle removal device 752 to the receiving position, the user can simply release the sliding members 782 and the one or more resilient members will move the sliding members 782 away from the base member 756.

The needle removal device 752 may include locking features configured to selectively lock the needle removal device 752 in the grasping position. For example, the sliding members 782 may include a plurality of teeth (not shown). The guide members 780 may include a plurality of teeth (not shown) configured to interlock with one or more of the teeth of the sliding members 782 when the needle removal device 752 is in the grasping position. Such a configuration may allow a user to conveniently and beneficially lock the needle removal device 752 in the grasping position. In other embodiments, the locking features may include one or more detents formed in the sliding members 782 and one or more grooves formed in the guide members 780 configured to engage the one or more detents when the needle removal device 752 is in the grasping position. In other embodiments, the locking features may be omitted.

As shown in FIG. 7A and FIG. 7B, the needle removal device 752 may include one or more needle receptacles 762 configured to receive the needles 708. The one or more needle receptacles 762 may be defined at least partially between the sliding members 782 and the base member 756. The one or more needle receptacles 762 may be configured and positioned to generally correspond to needle lumens 736 at the proximal end of the guide body 702. Such a configuration may allow the needles 708 to be received within the one or more needle receptacles 762 when the needles 708 exit the needle lumens 736. Such a configuration may allow a user to exert a force in the proximal direction on the needles 708 to overcome an initial resistance to removal of the needles 708 from the guide body 702. For example, in the grasping position, the needle removal device 752 may allow a user to exert a force in the proximal direction of about one quarter (0.25) pound-force to seventy (70) pound-force; about one (1) pound-force to sixty (60) pound-force; or about five (5) pound-force to forty (40) pound-force on the needles 708. In other embodiments, the needle removal device 752 may allow a user to exert larger or smaller forces on the needles 708. In yet other embodiments, the one or more needle receptacles 762 may include one or more gripping features configured to enhance the grip of the needle removal device 752 on the needles 708. For example, the one or more needle receptacles 762 may include textured surfaces, contoured surfaces, adhesives, magnets, or the like.

Figure 8C:
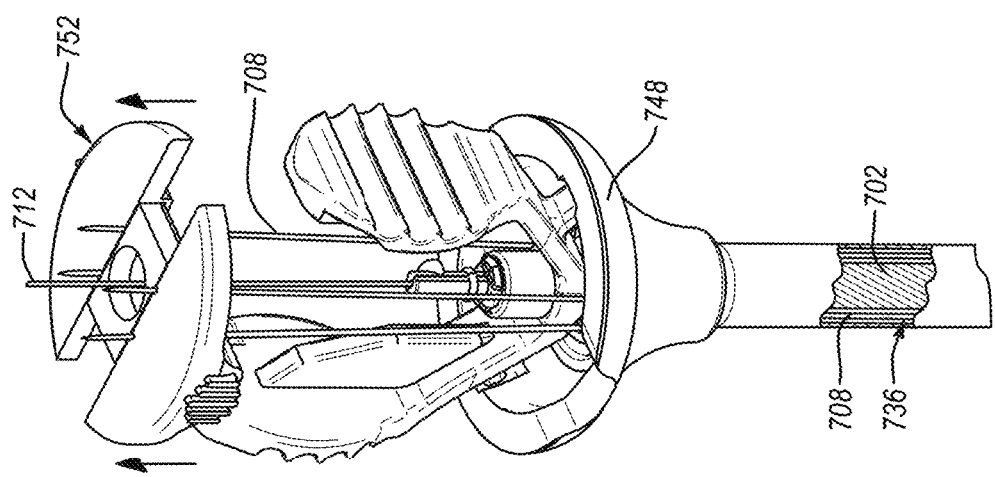
FIGS. 8A-8C illustrate exemplary steps for removing needles from the suturing system shown in FIG. 7A with the needle removal device.
Figure 8B:
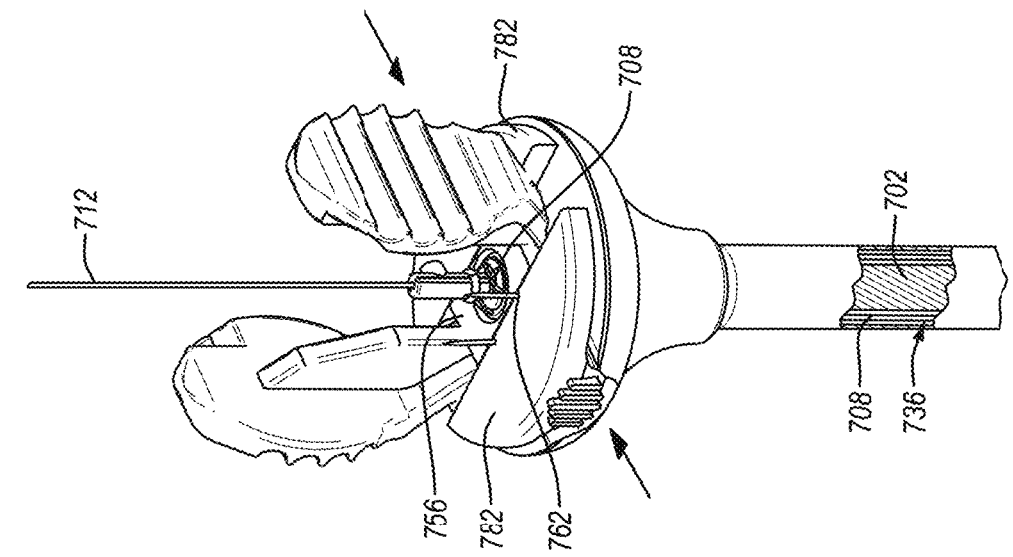
Figure 8A:
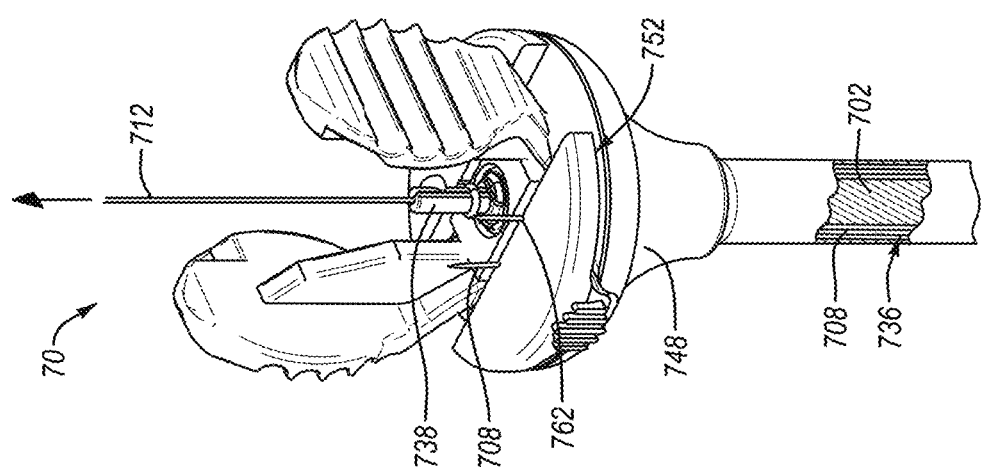

FIGS. 8A through 8C illustrate exemplary steps in a method for removing the needles 708 from the suturing system 70 with the needle removal device 752. While the method is illustrated using the suturing system 70 and the needle removal device 752, it will be appreciated that the described method may utilize any other needle removal device and/or suturing system disclosed herein. Only certain exemplary steps of removing the needles 708 from the suturing system 70 are shown and described, however, it will be appreciated that the method may follow delivery of needles and suture lengths through body tissue or a vessel wall by the suturing system 70. For example, the method may include any of the steps previously described and/or illustrated in relation to FIGS. 2A through 2D.

Referring now to FIG. 8A, to deploy the needles 708, the handle 718 (shown in FIG. 7A) may be drawn proximally relative to the guide body 702 to proximally move the needle deployment shaft 712. As shown, the needle deployment shaft 712 may draw the needles 708 proximally through the needle lumens 736 of the guide body 702 until the needles 708 exit the guide body 702 within the hub 748. As the needles 708 exit the guide body 702, the needles 708 may be received within the needle receptacles 762 while the needle removal device 752 is in the receiving position as shown.

Referring now to FIG. 8B, the sliding members 782 may be squeezed or pushed together toward the base member 756 to slidably move the needle removal device 752 into the grasping position. The sliding members 782 may be squeezed or pushed together with a user's fingers, a medical instrument, or any other suitable means. In the grasping position, the needles 708 may be grasped by the needle removal device 752 between the sliding members 782 and the base member 756 in the needle receptacles 762.

Referring now to FIG. 8C, with the needle removal device 752 in the grasping position, the needle removal device 752 may be moved proximally relative to the guide body 702. The needle removal device 752 may be configured to overcome an initial resistance to proximal movement of the needles 708 from the guide body 702. Proximal movement of the needle removal device 752, in turn, may continue to remove the needles 708 from the guide body 702. Once the needles 708 are removed from the guide body 702, suture lengths (not shown) attached to the needles 708 may be cut and the needles 708 may be disposed of. Such a configuration of the needle removal device 752 may allow a user to safely and securely remove the needles 708 from the suturing system 70.

Another embodiment of a needle removal device will now be described in relation to FIGS. 9A through 10C. A suturing system 90 may be similar in many respects to the suturing systems 10, 30, 50 and 70 previously described above in FIGS. 1A-8C. To the extent features or components of this configuration function in a manner similar to that as described above, such disclosure is hereby incorporated into the following additional configuration. Similar to suturing systems 30, 50, and 70, for ease of reference, only the proximal portion of the suturing system 90 is shown and described. The distal components may be manipulated by the proximal components in a similar manner as described with reference to FIGS. 1A through 8C.

Figure 9A:
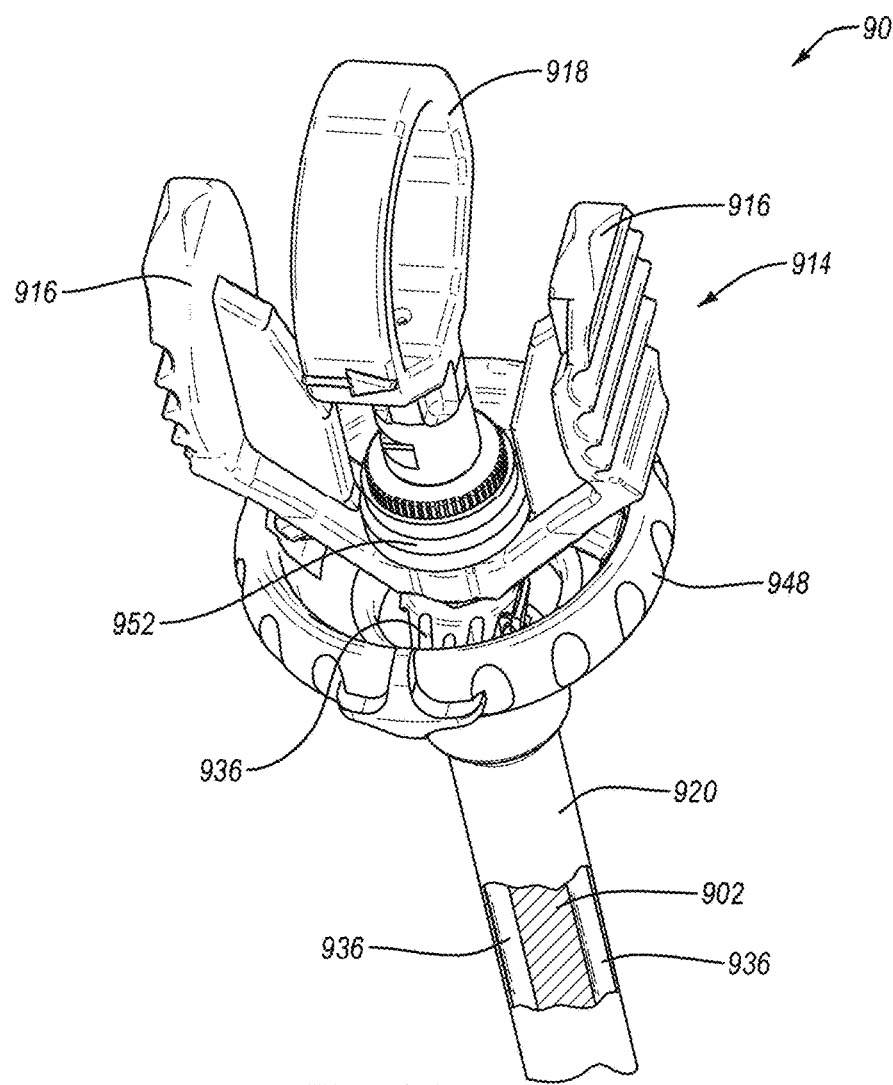
FIG. 9A is a partial side perspective view of a suturing system according to another embodiment.

FIG. 9A is a partial side perspective view of the suturing system 90. The suturing system 90 may include a guide body 902, a needle guide (not shown) secured to a distal end of the guide body 902, and a flexible tube (not shown) secured to a distal end of the needle guide. A sheath 920 may be rotatably received over the guide body 902. A plurality of needles 908 (shown in FIG. 10A) may be mounted with their distal ends in a support holster (not shown) and attached to a moveable needle deployment shaft 912 (shown in FIG. 10A). A handle assembly 914 may be attached to a proximal end of the guide body 902. The handle assembly 914 may include a pair of interlock wings 916, a needle removal device 952, and a handle 918. The handle 918 may be attached to a proximal end of the needle deployment shaft 912 and may be pulled proximally in order to draw the needles 908 from the flexible tube, through the needle guide and into the guide body 902 until the needles 908 emerge from the guide body 902 within a hub 948. Once the needles 908 emerge within the hub 948, the needles 908 may be received with the needle removal device 952.

Figure 9B:
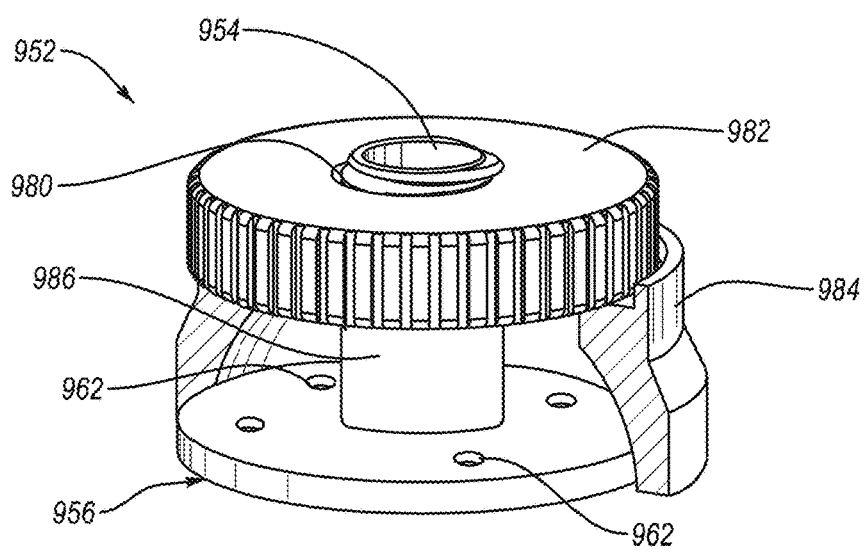
FIG. 9B is a perspective view of the needle removal device removed from the suturing system shown in FIG. 9A.

FIG. 9B is a partial cutaway isometric view of the needle removal device 952 removed from the suturing system 90. As shown, the needle removal device 952 may include a base member 956, a knob 982, and an outer casing 984. The base member 956 may have a generally cylindrical geometric shape and include a shaft 986 attached to an upper surface of the base member 956. A central aperture 954 may extend through the base member 956 and the shaft 986. The central aperture 954 may be configured to allow a stem 938 (shown in FIG. 10A) of the handle assembly 914 to pass through the base member 956 and the shaft 986 such that the needle removal device 952 may be selectively positioned between the guide body 902 and the handle 918. The central aperture 954 may also be configured to receive the needle deployment shaft 912 such that the needle deployment shaft may be selectively drawn through the base member 956 and the shaft 986. Such a configuration may allow the needle deployment shaft 912 and the needle removal device 952 to move axially relative to one another. The shaft 986 may include an outer threaded portion having a male or female thread.

As shown, a plurality of needle receptacles 962 may be formed in the base member 956 and extend therethrough. One or more of the needle receptacles 962 may have a generally cylindrical geometric shape, generally conical geometric shape, generally oval geometric shape, or any other suitable geometric shape. The needle receptacles 962 may be configured and positioned in the base member 956 to generally correspond to needle lumens 936 (shown in FIG. 9A) extending through the guide body 902. Such a configuration allows the needles 908 to be selectively received within the needle receptacles 962 when the needles 908 exit the needle lumens 936 of the guide body 902. While four needle receptacles 962 are shown formed in the base member 956, three, five, two, or any other suitable number of needle receptacles 962 may be formed in the base member 956 in any suitable configuration.

The knob 982 may have a generally cylindrical geometric shape and include an upper surface, a lower surface, and a side surface. The knob 982 may include ridges formed in the side surface configured to provide a user an improved grip on the knob 982. In other embodiments, the side surface of the knob 982 may include other features configured to improve the user's grip on the knob such as indentations for a user's fingers or tools or other suitable features.

The knob 982 may include an aperture 980. The aperture 980 may include an inner threaded portion with female or male thread configured to rotatably engage the outer threaded portion of the shaft 986. The base member 956 may move toward the knob 982 when the shaft 986 is threaded into the aperture of the knob 982 and the base member 956 may move away from the knob 982 when the shaft 986 is unthreaded from the aperture 980 of the knob 982.

The outer casing 984 may be attached to the bottom surface of the knob 982 and may be configured to at least partially receive the base member 956. The outer casing 984 may be rotatably attached to the knob 982 or the outer casing 984 may be integral and/or affixed to the knob 982. As shown, the outer casing 984 may include an inner surface having a first diameter in a distal portion that tapers proximally to a second diameter in a proximal portion.

At least a portion of the base member 956 may be formed of one or more substantially resilient materials such as polymers, polymeric composites, metals, combinations thereof, or the like. Configuring the base member 956 in this manner may allow the needle removal device 952 to move between a receiving position, wherein at least a portion of each needle 908 can pass through the needle receptacles 962, and a grasping position wherein the base member 956 may grasp or pinch the needles 908 within the needle receptacles 962. For example, in the receiving position the base member 956 may be positioned near the distal portion of the outer casing 984. Once needles 908 are received within the needle receptacles 962, the shaft 986 may be threaded through the knob 982 to move the knob 982 and the base member 956 closer to one another. As the base member 956 and the knob 982 move closer together, the tapered inner surface of the outer casing 984 may exert increasing external pressure on the base member 956 as the diameter of the inner surface of the outer casing 984 decreases. The external pressure on the base member 956 may in turn cause one or more of the needle receptacles 962 to deform or elongate such that a compression fit is formed between the needles 908 and the needle receptacles 962. The needle removal device 952 may be configured to allow a user to exert a force in the proximal direction on the needles 908 to overcome an initial resistance to removal of the needles 908 from the guide body 902. For example, in the grasping position, the needle removal device 952 may allow a user to exert a force in the proximal direction of about one quarter (0.25) pound-force to seventy (70) pound-force; about one (1) pound-force to sixty (60) pound-force; or about five (5) pound-force to forty (40) pound-force on the needles 908 to overcome an initial resistance to proximal movement of the needles 908 from the guide body 902. In other embodiments, the needle removal device 952 may allow a user to exert larger or smaller forces on the needles 908.

FIGS. 10A through 10C illustrate exemplary steps in a method for removing the needles 908 from the suturing system 90 with the needle removal element 952. While the method is illustrated using the suturing system 90 and the needle removal device 952, it will be appreciated that the described method may utilize any other needle removal device and/or suturing system disclosed herein. Only certain exemplary steps of removing the needles 908 from the suturing system 90 are shown and described, however, it will be appreciated that the method may follow delivery of needles and suture lengths through body tissue or a vessel wall by the suturing system 90. For example, the method may include any of the steps previously described and/or illustrated in relation to FIGS. 2A through 2D.

Referring now to FIG. 10A, to deploy the needles 908, the handle 918 (shown in FIG. 9A) may be drawn proximally relative to the guide body 902 to proximally move the needle deployment shaft 912. As shown, the needle deployment shaft 912 may draw the needles 908 proximally through the needle lumens 936 of the guide body 902 until the needles 908 exit the guide body 902 within the hub 948. As the needles 908 exit the guide body 902, the needles 908 may be received within the needle receptacles 962 with the needle removal device 952 in the receiving position as shown. As shown, tips of the needles 908 may be received and positioned within the needle removal device 952 such that risk of injury to the user or a patient is reduced.

Referring now to FIG. 10B, the knob 982 may be rotated relative to the shaft such that the base member 956 and the knob 982 move closer together. As the base member 956 and the knob 982 move closer together, the needle removal device 952 may move into the grasping position. Specifically, as the base member 956 and the knob 982 move closer together, the inner surface of the outer casing 984 may exert an increasing external pressure on the base member 956 such that the needle receptacles 962 deform to create a compression fit between the needles 908 and the needle receptacles 962. If a user desires to increase the strength of the compression fit, the user may continue to move the knob 982 and the base member 956 closer together such that the external pressure on the base member 956 increases. Accordingly, a user may control the grasping strength of the needle removal device 952 on the needles 908 with relative rotation between the knob 982 and the base member 956.

Referring now to FIG. 10C, with the needle removal device 952 in the grasping position, the needle removal device 952 may be moved proximally relative to the guide body 902. Proximal movement of the needle removal device 952, in turn, may continue to remove the needles 908 from the guide body 902. The compression fit between the needles 908 and the needle receptacles 962 may be configured to overcome an initial resistance to proximal movement of the needles 908 from the guide body 902. Once the needles 908 are removed from the guide body 902, suture lengths (not shown) attached to the needles 908 may be cut and the needles 908 may be disposed of. Such a configuration of the needle removal device 752 may allow a user to safely and securely remove the needles 708 from the suturing system 70.

In yet other embodiments, needle removal devices may be configured to secure needles for removal from suturing systems by at least partially deforming the needles as described in U.S. Patent Application, entitled "Needle Harvesting Devices, Systems and Methods," Ser. No. 13/610,602, filed on the same day, the disclosure of which is incorporated herein in its entirety.

Embodiments of the suturing device, needle removal device and the like may include a material made from any of a variety of known suitable biocompatible materials, such as a biocompatible shape memory material (SMM). For example, the SMM may be shaped in a manner that allows for the needle removal device to automatically move from the receiving position to the grasping position when needles are received within the needle receptacles. SMMs have a shape memory effect in which they may be made to remember a particular shape. Once a shape has been remembered, the SMM may be bent out of shape or deformed and then returned to its original shape by unloading from strain or heating. Typically, SMMs may be shape memory alloys (SMA) comprised of metal alloys, or shape memory plastics (SMP) comprised of polymers. The materials may also be referred to as being superelastic.

Usually, an SMA may have an initial shape that may then be configured into a memory shape by heating the SMA and conforming the SMA into the desired memory shape. After the SMA is cooled, the desired memory shape may be retained. This allows for the SMA to be bent, straightened, twisted, compacted, and placed into various contortions by the application of requisite forces; however, after the forces are released, the SMA may be capable of returning to the memory shape. The main types of SMAs are as follows: copper-zinc-aluminum; copper-aluminum-nickel; nickel-titanium (NiTi) alloys known as nitinol; nickel-titanium platinum; nickel-titanium palladium; and cobalt-chromium-nickel alloys or cobalt-chromium-nickel-molybdenum alloys known as elgiloy alloys. The temperatures at which the SMA changes its crystallographic structure are characteristic of the alloy, and may be tuned by varying the elemental ratios or by the conditions of manufacture.

For example, the primary material of needle removal device may be of a NiTi alloy that forms superelastic nitinol. Also, additional materials may be added to the nitinol depending on the desired characteristic. The alloy may be utilized having linear elastic properties or non-linear elastic properties.

An SMP is a shape-shifting plastic that may be fashioned into the needle receptacles of the base member in accordance with the present disclosure. Also, it may be beneficial to include at least one layer of an SMA and at least one layer of an SMP to form a multilayered body; however, any appropriate combination of materials may be used to form a multilayered device. When an SMP encounters a temperature above the lowest melting point of the individual polymers, the blend makes a transition to a rubbery state. The elastic modulus may change more than two orders of magnitude across the transition temperature (Ttr). As such, an SMP may be formed into a desired shape of an endoprosthesis by heating it above the Ttr, fixing the SMP into the new shape, and cooling the material below Ttr. The SMP may then be arranged into a temporary shape by force and then resume the memory shape once the force has been released. Examples of SMPs include, but are not limited to, biodegradable polymers, such as oligo(ε-caprolactone)diol, oligo(p-dioxanone)diol, and non-biodegradable polymers such as, polynorborene, polyisoprene, styrene butadiene, polyurethane-based materials, vinyl acetate-polyester-based compounds, and others yet to be determined. As such, any SMP may be used in accordance with the present disclosure.

The needle receptacles and the like may have at least one layer made of an SMM or suitable superelastic material and other suitable layers that can allow the needle receptacles to automatically grasp onto the needles.

Also, the needle removal devices, the needle receptacles or other aspects or components of the system may be comprised of a variety of known suitable deformable materials, including stainless steel, silver, platinum, tantalum, palladium, nickel, titanium, nitinol, nitinol having tertiary materials (U.S. 2005/0038500, which is incorporated herein by reference, in its entirety), niobium-tantalum alloy optionally doped with a tertiary material (U.S. 2004/0158309, 2007/0276488, and 2008/0312740, which are each incorporated herein by reference, in their entireties) cobalt-chromium alloys, or other known biocompatible materials. Such biocompatible materials may include a suitable biocompatible polymer in addition to or in place of a suitable metal. The polymeric needle removal device may include biodegradable or bioabsorbable materials.

In one embodiment, the needle removal device and/or needle receptacles may be made from a superelastic alloy such as nickel-titanium or nitinol, and includes a ternary element selected from the group of chemical elements consisting of iridium, platinum, gold, rhenium, tungsten, palladium, rhodium, tantalum, silver, ruthenium, or hafnium. The added ternary element improves the radiopacity of the nitinol knot replacement element. The nitinol needle removal device has improved radiopacity yet retains its superelastic and shape memory behavior and further maintains a thin body thickness for high flexibility.

In one embodiment, the needle removal device and/or the needle receptacles may be made at least in part of a high strength, low modulus metal alloy comprising Niobium, Tantalum, and at least one element selected from the group consisting of Zirconium, Tungsten, and Molybdenum.

In further embodiments, the needle removal device and/or the needle receptacles may be made from or be coated with a biocompatible polymer. Examples of such biocompatible polymeric materials may include hydrophilic polymer, hydrophobic polymer, biodegradable polymers, bioabsorbable polymers, and monomers thereof. Examples of such polymers may include nylons, poly(alpha-hydroxy esters), polylactic acids, polylactides, poly-L-lactide, poly-DL-lactide, poly-L-lactide-co-DL-lactide, polyglycolic acids, polyglycolide, polylactic-co-glycolic acids, polyglycolide-co-lactide, polyglycolide-co-DL-lactide, polyglycolide-co-L-lactide, polyanhydrides, polyanhydride-co-imides, polyesters, polyorthoesters, polycaprolactones, polyesters, polyanydrides, polyphosphazenes, polyester amides, polyester urethanes, polycarbonates, polytrimethylene carbonates, polyglycolide-co-trimethylene carbonates, poly(PB A-carbonates), polyfumarates, polypropylene fumarate, poly(p-dioxanone), polyhydroxyalkanoates, polyamino acids, poly-L-tyrosines, poly(beta-hydroxybutyrate), polyhydroxybutyrate-hydroxyvaleric acids, polyethylenes, polypropylenes, polyaliphatics, polyvinylalcohols, polyvinylacetates, hydrophobic/hydrophilic copolymers, alkylvinylalcohol copolymers, ethylenevinylalcohol copolymers (EVAL), propylenevinylalcohol copolymers, polyvinylpyrrolidone (PVP), combinations thereof, polymers having monomers thereof, or the like.

The coatings can also be provided on the system or components thereof to facilitate the loading or delivery of beneficial agents or drugs, such as therapeutic agents, pharmaceuticals and radiation therapies.

The invention is susceptible to various modifications and alternative means, and specific examples thereof have been shown by way of example in the drawings and are herein described in detail. It should be understood, however, that the invention is not to be limited to the particular systems or methods disclosed, but to the contrary; the invention is to cover all modifications, equivalents, and alternatives falling within the spirit and scope of the claims.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A medical device comprising:
    an elongate member extending from a proximal end toward a distal end, the elongate member having a lumen with a longitudinal axis;
    a first proximal assembly towards the proximal end of the elongate member;
    a second proximal assembly cooperating with the first proximal assembly, the second proximal assembly comprising:
        a base portion comprising a groove having a gap and an opening, the base portion being configured to cooperate with a portion of the first proximal assembly; and
        two wings being opposite sides of the base portion, the two wings being configured to move in relation to the longitudinal axis of the elongate member to change the gap of the groove, the two wings extending from a proximal end of the first proximal assembly.

2. The medical device of claim 1, wherein each wing has an elongate slot having a closed first end at a location between the base portion and a peripheral end of the wing.

3. The medical device of claim 1, wherein each of the two wings include a textured surface.

4. A method of forming a medical device comprising:
    providing a first medical device portion comprising:
        an elongate member;
        a stem disposed towards a proximal end of the first medical device portion and proximal the elongate member, the stem comprising a protruding portion extending from one side of a stem portion; and
        a lumen extending through the elongate member and the stem; and
    positioning a second medical device portion over the stem so that the second medical device portion at least partially surrounds a portion of the first medical device portion, the second medical device portion comprising:
        a base portion with a groove having a gap; and
        two wings extending from the base portion, the wings being opposite each other on opposite sides of the base portion, the two wings being configured to move in relation to the longitudinal axis to change the gap of the groove.

5. The method of claim 4, wherein positioning the second medical device portion over the stem, further comprises mounting the second medical device portion to the stem of the first medical device portion.

6. The method of claim 4, wherein the base portion is formed of a polymer.

7. The method of claim 4, wherein each wing of the two wings comprises a first portion angularly orientated in relation to a second portion, the second portion extending to and forming the peripheral end.

8. The method of claim 7, wherein the elongate slot of each wing extending over at least a portion of each of the first portion and the second portion.

9. The method of claim 4, wherein each of the two wings include a textured surface.

10. The method of claim 4, wherein each of the two wings include ridges.

11. The method of claim 4, wherein the base portion further comprises a second groove disposed from the first groove by an opening.

12. The method of claim 4, wherein the two wings are integral with the base portion.

13. The method of claim 4, wherein the stem comprises a slot.

* * * * *